US011851490B2

(12) United States Patent
Kan et al.

(10) Patent No.: US 11,851,490 B2
(45) Date of Patent: Dec. 26, 2023

(54) METHODS AND COMPOSITIONS FOR TREATING, INHIBITING, AND/OR PREVENTING HETEROTOPIC OSSIFICATION

(71) Applicant: Northwestern University, Evanston, IL (US)

(72) Inventors: Lixin Kan, Chicago, IL (US); John A. Kessler, Chicago, IL (US)

(73) Assignee: Northwestern University, Evanston, IL (US)

( * ) Notice: Subject to any disclaimer, the term of this patent is extended or adjusted under 35 U.S.C. 154(b) by 426 days.

(21) Appl. No.: 16/995,392

(22) Filed: Aug. 17, 2020

(65) Prior Publication Data

US 2021/0047413 A1 Feb. 18, 2021

Related U.S. Application Data

(60) Provisional application No. 62/887,079, filed on Aug. 15, 2019.

(51) Int. Cl.
*A61K 39/395* (2006.01)
*C07K 16/28* (2006.01)
*A61P 19/00* (2006.01)
*A61K 38/16* (2006.01)
*A61K 38/17* (2006.01)

(52) U.S. Cl.
CPC .......... *C07K 16/2818* (2013.01); *A61K 38/16* (2013.01); *A61P 19/00* (2018.01); *C07K 16/2827* (2013.01); *A61K 38/1741* (2013.01); *A61K 39/395* (2013.01)

(58) Field of Classification Search
None
See application file for complete search history.

(56) References Cited

U.S. PATENT DOCUMENTS

| | | | | |
|---|---|---|---|---|
| 5,288,931 A | * | 2/1994 | Chang | C07K 1/1133 530/825 |
| 7,112,660 B1 | * | 9/2006 | Domingues | A61P 37/08 424/85.2 |
| 2003/0045474 A1 | * | 3/2003 | Sailer | A61K 38/1875 514/8.8 |
| 2012/0328615 A1 | * | 12/2012 | Romagne | A61P 37/02 424/131.1 |
| 2014/0154743 A1 | * | 6/2014 | Levy | C12Y 502/01008 435/69.6 |

FOREIGN PATENT DOCUMENTS

| | | |
|---|---|---|
| WO | 2001014424 A2 | 3/2001 |
| WO | 2013173223 A1 | 11/2013 |
| WO | 2016137985 A1 | 9/2016 |

OTHER PUBLICATIONS

Weber (2010, Semin Oncol 37:430-439).*
Saleh et al. (2019, Cancer Lett 457:168-179).*
Tokuriki et al., 2009, Curr. Opin. Struc. Biol. 19:596-604).*
Fenton et al. (2020, Medicinal Chemistry Research 29:1133-1146).*
Bhattacharya et al. (2017, PLoS ONE 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Duval et al. (2007, J Can Dent Assoc 73:845-850).*
Agarwal S, et al. Scleraxis-Lineage Cells Contribute to Ectopic Bone Formation in Muscle and Tendon. Stem Cells. 2017;35(3):705-10.
Cicerone C, et al. Th17, intestinal microbiota and the abnormal immune response in the pathogenesis of celiac disease. Gastroenterol Hepatol Bed Bench. 2015;8(2):117-22.
Convente MR, et al. Depletion of Mast Cells and Macrophages Impairs Heterotopic Ossification in an Acvr1R206H Mouse Model of Fibrodysplasia Ossificans Progressiva. J Bone Miner Res. 201833(2):269-282.
Crowgey EL, et al. A Systems Biology Approach for Studying Heterotopic Ossification: Proteomic Analysis of Clinical Serum and Tissue Samples. Genomics Proteomics Bioinformatics. Jun. 2018;16(3):212-220.
Czura CJ, et al. Neural inhibition of inflammation: the cholinergic anti-inflammatory pathway. J Endotoxin Res. 2003;9(6):409-13.
Davis EL, et al. Location-dependent heterotopic ossification in the rat model: The role of activated matrix metalloproteinase 9. J Orthop Res. Nov. 2016;34(11):1894-1904.
Dey D, et al. The traumatic bone: trauma-induced heterotopic ossification. Transl Res. 2017;186:95-111.
Haupt J, et al. ACVR1R206H FOP mutation alters mechanosensing and tissue stiffness during heterotopic ossification. Mol Biol Cell. 2019;30(1):17-29.
Huning I, et al. Fibrodysplasia ossificans progressiva: clinical course, genetic mutations and genotype-phenotype correlation. Mol Syndromol. 2014;5(5):201-11.
Hurlimann M, et al. Influence of surgical approach on heterotopic ossification after total hip arthroplasty—is minimal Invasive better? A case control study. BMC Musculoskelet Disord. 2017;18(1):27.

(Continued)

*Primary Examiner* — Elizabeth C. Kemmerer
(74) *Attorney, Agent, or Firm* — QUARLES & BRADY LLP

(57) ABSTRACT

Disclosed are methods and compositions for treating, inhibiting, and/or preventing heterotopic ossification in a subject in need thereof. Particularly disclosed are methods for treating, inhibiting, and/or preventing heterotopic ossification in a subject in need thereof by administering to the subject a therapeutic agent such as an immune checkpoint inhibitor and/or Fetuin-A or a variant thereof. Also disclosed are pharmaceutical compositions and pharmaceutical kits comprising an immune checkpoint inhibitor and/or Fetuin-A or a variant thereof for treating, inhibiting, and/or preventing heterotopic ossification in a subject in need thereof.

13 Claims, 29 Drawing Sheets

Specification includes a Sequence Listing.

(56) References Cited

OTHER PUBLICATIONS

Jasiulionis MG. Abnormal Epigenetic Regulation of Immune System during Aging. Front Immunol. 2018;9:197.
Jiang JX. Posttraumatic stress and immune dissonance. Chin J Traumatol. 2008;11(4):203-8.
Jung K, et al. Emerging Co-signaling Networks in T Cell Immune Regulation. Immune Netw. 2013;13(5):184-93.
Kan C, et al. Gli1-labeled adult mesenchymal stem/progenitor cells and hedgehog signaling contribute to endochondral heterotopic ossification. Bone. 2018.
Kan C, et al. Conserved signaling pathways underlying heterotopic ossification. Bone. 2018.
Kan C, et al. BMP-dependent, injury-induced stem cell niche as a mechanism of heterotopic ossification. Stem Cell Res Ther. 2019;10(1):14.
Kan et al., "Inhibition of immune checkpoints prevents injury-induced heterotopic ossification," Bone Res. 2019; 7; 33; pp. 1-8.
Kan L, et al. Transgenic mice overexpressing BMP4 develop a fibrodysplasia ossificans progressiva (FOP)-like phenotype. Am J Pathol. 2004;165(4):1107-15.
Kan L, et al. Evaluation of the cellular origins of heterotopic ossification. Orthopedics. 2014;37(5):329-40.
Kan L, et al. Dysregulation of local stem/progenitor cells as a common cellular mechanism for heterotopic ossification. Stem Cells. 2009;27(1):150-6.
Kan L, et al. Substance P signaling mediates BMP-dependent heterotopic ossification. J Cell Biochem. 2011;112(10):2759-72.
Kan L, et al. Opioid signaling in mast cells regulates injury responses associated with heterotopic ossification. Inflamm Res. 2014;63(3):207-15.
Kan L, et al. Glast-expressing progenitor cells contribute to heterotopic ossification. Bone. 2013;53(1):194-203.
Kaplan, F. S., et al. Granting immunity to FOP and catching heterotopic ossification in the Act. Semin. Cell Dev. Biol. 49, 30-36 (2016).
Kohn J. Abnormal immune response in burns. Postgrad Med J. 1972;48(560):335-7.
Kraft CT, et al. Trauma-induced heterotopic bone formation and the role of the immune system: A review. J Trauma Acute Care Surg. Jan. 2016;80(1):156-65.
Legosz P, et al. Challenges of heterotopic ossification-Molecular background and current treatment strategies. Clin Exp Pharmacol Physiol. 2018;45(12):1229-35.
Levesque JP, et al. Macrophages Driving Heterotopic Ossification: Convergence of Genetically-Driven and Trauma-Driven Mechanisms. J Bone Miner Res. 2018;33(2):365-366.
Loder SJ, et al. Characterizing the Circulating Cell Populations in Traumatic Heterotopic Ossification Am J Pathol. 2018; 188(11):2464-2473.
Meyers C, et al. Heterotopic Ossification: A Comprehensive Review. JBMR Plus. 2019;3(4):e10172.
Pacifici M. Acquired and congenital forms of heterotopic ossification: new pathogenic insights and therapeutic opportunities. Curr Opin Pharmacol. 2018;40:51-8.
Qureshi AT, et al. Inhibition of Mammalian Target of Rapamycin Signaling with Rapamycin Prevents Trauma-Induced Heterotopic Ossification. Am J Pathol. 2017;187(11):2536-45.
Ranganathan K, et al. The role of the adaptive immune system in burn-induced heterotopic ossification and mesenchymal cell osteogenic differentiation. J Surg Res. 2016;206(1):53-61.
Riva A, et al. Immune checkpoint receptors: homeostatic regulators of immunity. Hepatol Int. 2018.
Rodenberg E, et al. Matrix metalloproteinase-9 is a diagnostic marker of heterotopic ossification in a murine model. Tissue Eng Part A (2011) 17:2487-96. 10.1089/ten.tea.2011.00.
Sakellariou VI, et al. Heterotopic ossification following traumatic brain injury and spinal cord injury: insight into the etiology and pathophysiology. J Musculoskelet Neuronal Interact. 2012;12(4):230-40.
Sperk M, et al. Immune Checkpoints as the Immune System Regulators and Potential Biomarkers in HIV-1 Infection. Int J Mol Sci. 2018;19(7).
Wang H, et al. "Activin A amplifies dysregulated BMP signaling and induces chondro-osseous differentiation of primary connective tissue progenitor cells in patients with fibrodysplasia ossificans progressiva (FOP)." Bone 109 (2018): 218-224.
Wendel A, et al. Ebselen-an in vivo immune response modifier. Biomed Environ Sci. 1997;10(2-3):253-9.
Xu R, et al. "Heterotopic ossification: mechanistic insights and clinical challenges." Bone 109 (2018): 134-142.
Zeckey C, et al. Heterotopic ossifications following implant surgery-epidemiology, therapeutical approaches and current concepts. Semin Immunopathol. 2011;33(3):273-86.

\* cited by examiner

SEQUENCE LISTING

```
<160> NUMBER OF SEQ ID NOS: 6

<210> SEQ ID NO 1
<211> LENGTH: 368
<212> TYPE: PRT
<213> ORGANISM: Homo sapiens

<400> SEQUENCE: 1

Met Lys Ser Leu Val Leu Leu Leu Cys Leu Ala Gln Leu Trp Gly Cys
1               5                   10                  15

His Ser Ala Pro His Gly Pro Gly Leu Ile Tyr Arg Gln Pro Asn Cys
            20                  25                  30

Asp Asp Pro Glu Thr Glu Glu Ala Ala Leu Val Ala Ile Asp Tyr Ile
```

```
                35                  40                  45
Asn Gln Asn Leu Pro Trp Gly Tyr Lys His Thr Leu Asn Gln Ile Asp
        50                  55                  60

Glu Val Lys Val Trp Pro Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Ala Asp Ser Ala Glu Asp Val Arg
    130                 135                 140

Lys Val Cys Gln Asp Cys Pro Leu Leu Ala Pro Leu Asn Asp Thr Arg
145                 150                 155                 160

Val Val His Ala Ala Lys Ala Ala Leu Ala Ala Phe Asn Ala Gln Asn
                165                 170                 175

Asn Gly Ser Asn Phe Gln Leu Glu Glu Ile Ser Arg Ala Gln Leu Val
            180                 185                 190

Pro Leu Pro Pro Ser Thr Tyr Val Glu Phe Thr Val Ser Gly Thr Asp
        195                 200                 205

Cys Val Ala Lys Glu Ala Thr Glu Ala Ala Lys Cys Asn Leu Leu Ala
    210                 215                 220

Glu Lys Gln Tyr Gly Phe Cys Lys Ala Thr Leu Ser Glu Lys Leu Gly
225                 230                 235                 240

Gly Ala Glu Val Ala Val Thr Cys Met Val Phe Gln Thr Gln Pro Val
                245                 250                 255

Ser Ser Gln Pro Gln Pro Glu Gly Ala Asn Glu Ala Val Pro Thr Pro
            260                 265                 270

Val Val Asp Pro Asp Ala Pro Pro Ser Pro Leu Gly Ala Pro Gly
        275                 280                 285

Leu Pro Pro Ala Gly Ser Pro Pro Asp Ser His Val Leu Leu Ala Ala
    290                 295                 300

Pro Pro Gly His Gln Leu His Arg Ala His Tyr Asp Leu Arg His Thr
305                 310                 315                 320

Phe Met Gly Val Val Ser Leu Gly Ser Pro Ser Gly Glu Val Ser His
                325                 330                 335

Pro Arg Lys Thr Arg Thr Val Val Gln Pro Ser Val Gly Ala Ala Ala
            340                 345                 350

Gly Pro Val Val Pro Pro Cys Pro Gly Arg Ile Arg His Phe Lys Val
        355                 360                 365

<210> SEQ ID NO 2
<211> LENGTH: 367
<212> TYPE: PRT
<213> ORGANISM: Homo sapiens

<400> SEQUENCE: 2

Met Lys Ser Leu Val Leu Leu Cys Leu Ala Gln Leu Trp Gly Cys
1               5                   10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45
```

```
Asn Gln Asn Leu Pro Trp Gly Tyr Lys His Thr Leu Asn Gln Ile Asp
     50                  55                  60
Glu Val Lys Val Trp Pro Gln Gln Pro Ser Gly Glu Leu Phe Glu Ile
 65                  70                  75                  80
Glu Ile Asp Thr Leu Glu Thr Thr Cys His Val Leu Asp Pro Thr Pro
                 85                  90                  95
Val Ala Arg Cys Ser Val Arg Gln Leu Lys Glu His Ala Val Glu Gly
            100                 105                 110
Asp Cys Asp Phe Gln Leu Leu Lys Leu Asp Gly Lys Phe Ser Val Val
            115                 120                 125
Tyr Ala Lys Cys Asp Ser Ser Pro Asp Ser Ala Glu Asp Val Arg Lys
        130                 135                 140
Val Cys Gln Asp Cys Pro Leu Leu Ala Pro Leu Asn Asp Thr Arg Val
145                 150                 155                 160
Val His Ala Ala Lys Ala Ala Leu Ala Ala Phe Asn Ala Gln Asn Asn
                    165                 170                 175
Gly Ser Asn Phe Gln Leu Glu Glu Ile Ser Arg Ala Gln Leu Val Pro
            180                 185                 190
Leu Pro Pro Ser Thr Tyr Val Glu Phe Thr Val Ser Gly Thr Asp Cys
            195                 200                 205
Val Ala Lys Glu Ala Thr Glu Ala Ala Lys Cys Asn Leu Leu Ala Glu
        210                 215                 220
Lys Gln Tyr Gly Phe Cys Lys Ala Thr Leu Ser Glu Lys Leu Gly Gly
225                 230                 235                 240
Ala Glu Val Ala Val Thr Cys Met Val Phe Gln Thr Gln Pro Val Ser
                    245                 250                 255
Ser Gln Pro Gln Pro Glu Gly Ala Asn Glu Ala Val Pro Thr Pro Val
            260                 265                 270
Val Asp Pro Asp Ala Pro Pro Ser Pro Pro Leu Gly Ala Pro Gly Leu
            275                 280                 285
Pro Pro Ala Gly Ser Pro Pro Asp Ser His Val Leu Leu Ala Ala Pro
        290                 295                 300
Pro Gly His Gln Leu His Arg Ala His Tyr Asp Leu Arg His Thr Phe
305                 310                 315                 320
Met Gly Val Val Ser Leu Gly Ser Pro Ser Gly Glu Val Ser His Pro
                    325                 330                 335
Arg Lys Thr Arg Thr Val Val Gln Pro Ser Val Gly Ala Ala Ala Gly
            340                 345                 350
Pro Val Pro Pro Cys Pro Gly Arg Ile Arg His Phe Lys Val
        355                 360                 365

<210> SEQ ID NO 3
<211> LENGTH: 366
<212> TYPE: PRT
<213> ORGANISM: Homo sapiens

<400> SEQUENCE: 3

Met Lys Ser Leu Val Leu Leu Cys Leu Ala Gln Leu Trp Gly Cys
 1               5                  10                  15
His Ser Ala Pro His Gly Pro Gly Leu Ile Tyr Arg Gln Pro Asn Cys
                 20                  25                  30
Asp Asp Pro Glu Thr Glu Glu Ala Ala Leu Val Ala Ile Asp Tyr Ile
            35                  40                  45
Asn Gln Asn Leu Pro Trp Gly Tyr Lys His Thr Leu Asn Gln Ile Asp
        50                  55                  60
```

Glu Val Lys Val Trp Pro Gln Pro Ser Gly Glu Leu Phe Glu Ile Glu
65              70                  75                  80

Ile Asp Thr Leu Glu Thr Thr Cys His Val Leu Asp Pro Thr Pro Val
                85                  90                  95

Ala Arg Cys Ser Val Arg Gln Leu Lys Glu His Ala Val Glu Gly Asp
            100                 105                 110

Cys Asp Phe Gln Leu Leu Lys Leu Asp Gly Lys Phe Ser Val Val Tyr
        115                 120                 125

Ala Lys Cys Asp Ser Ser Pro Asp Ser Ala Glu Asp Val Arg Lys Val
130                 135                 140

Cys Gln Asp Cys Pro Leu Leu Ala Pro Leu Asn Asp Thr Arg Val Val
145                 150                 155                 160

His Ala Ala Lys Ala Ala Leu Ala Ala Phe Asn Ala Gln Asn Asn Gly
                165                 170                 175

Ser Asn Phe Gln Leu Glu Glu Ile Ser Arg Ala Gln Leu Val Pro Leu
            180                 185                 190

Pro Pro Ser Thr Tyr Val Glu Phe Thr Val Ser Gly Thr Asp Cys Val
        195                 200                 205

Ala Lys Glu Ala Thr Glu Ala Ala Lys Cys Asn Leu Leu Ala Glu Lys
210                 215                 220

Gln Tyr Gly Phe Cys Lys Ala Thr Leu Ser Glu Lys Leu Gly Gly Ala
225                 230                 235                 240

Glu Val Ala Val Thr Cys Met Val Phe Gln Thr Gln Pro Val Ser Ser
                245                 250                 255

Gln Pro Gln Pro Glu Gly Ala Asn Glu Ala Val Pro Thr Pro Val Val
            260                 265                 270

Asp Pro Asp Ala Pro Pro Ser Pro Leu Gly Ala Pro Gly Leu Pro
        275                 280                 285

Pro Ala Gly Ser Pro Pro Asp Ser His Val Leu Leu Ala Ala Pro Pro
290                 295                 300

Gly His Gln Leu His Arg Ala His Tyr Asp Leu Arg His Thr Phe Met
305                 310                 315                 320

Gly Val Val Ser Leu Gly Ser Pro Ser Gly Glu Val Ser His Pro Arg
                325                 330                 335

Lys Thr Arg Thr Val Val Gln Pro Ser Val Gly Ala Ala Ala Gly Pro
            340                 345                 350

Val Val Pro Pro Cys Pro Gly Arg Ile Arg His Phe Lys Val
        355                 360                 365

<210> SEQ ID NO 4
<211> LENGTH: 339
<212> TYPE: PRT
<213> ORGANISM: Homo sapiens

<400> SEQUENCE: 4

Met Lys Ser Leu Val Leu Leu Leu Cys Leu Ala Gln Leu Trp Gly Cys
1               5                   10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
        50                  55                  60

Glu Val Lys Val Trp Pro Gln Gln Pro Ser Gly Glu Leu Phe Glu Ile

```
                65                  70                  75                  80
        Glu Ile Asp Thr Leu Glu Thr Thr Cys His Val Leu Asp Pro Thr Pro
                        85                  90                  95

Val Ala Arg Cys Ser Val Arg Gln Leu Lys Glu His Ala Val Glu Gly
                        100                 105                 110

Asp Cys Asp Phe Gln Leu Leu Lys Leu Asp Gly Lys Phe Ser Val Val
                        115                 120                 125

Tyr Ala Lys Cys Asp Ser Ser Pro Asp Ser Ala Glu Asp Val Arg Lys
                        130                 135                 140

Val Cys Gln Asp Cys Pro Leu Leu Ala Pro Leu Asn Asp Thr Arg Val
        145                 150                 155                 160

Val His Ala Ala Lys Ala Ala Leu Ala Ala Phe Asn Ala Gln Asn Asn
                        165                 170                 175

Gly Ser Asn Phe Gln Leu Glu Glu Ile Ser Arg Ala Gln Leu Val Pro
                        180                 185                 190

Leu Pro Pro Ser Thr Tyr Val Glu Phe Thr Val Ser Gly Thr Asp Cys
                        195                 200                 205

Val Ala Lys Glu Ala Thr Glu Ala Ala Lys Cys Asn Leu Leu Ala Glu
                        210                 215                 220

Lys Pro Val Ser Ser Gln Pro Gln Pro Glu Gly Ala Asn Glu Ala Val
        225                 230                 235                 240

Pro Thr Pro Val Val Asp Pro Asp Ala Pro Ser Pro Pro Leu Gly
                        245                 250                 255

Ala Pro Gly Leu Pro Pro Ala Gly Ser Pro Pro Asp Ser His Val Leu
                        260                 265                 270

Leu Ala Ala Pro Pro Gly His Gln Leu His Arg Ala His Tyr Asp Leu
                        275                 280                 285

Arg His Thr Phe Met Gly Val Val Ser Leu Gly Ser Pro Ser Gly Glu
                        290                 295                 300

Val Ser His Pro Arg Lys Thr Arg Thr Val Val Gln Pro Ser Val Gly
        305                 310                 315                 320

Ala Ala Ala Gly Pro Val Val Pro Pro Cys Pro Gly Arg Ile Arg His
                        325                 330                 335

Phe Lys Val

<210> SEQ ID NO 5
<211> LENGTH: 359
<212> TYPE: PRT
<213> ORGANISM: Bos taurus

<400> SEQUENCE: 5

Met Lys Ser Phe Val Leu Leu Phe Cys Leu Ala Gln Leu Trp Gly Cys
        1               5                   10                  15

His Ser Ile Pro Leu Asp Pro Val Ala Gly Tyr Lys Glu Pro Ala Cys
                        20                  25                  30

Asp Asp Pro Asp Thr Glu Gln Ala Ala Leu Ala Ala Val Asp Tyr Ile
                        35                  40                  45

Asn Lys His Leu Pro Arg Gly Tyr Lys His Thr Leu Asn Gln Ile Asp
                        50                  55                  60

Ser Val Lys Val Trp Pro Arg Arg Pro Thr Gly Glu Val Tyr Asp Ile
        65                  70                  75                  80

Glu Ile Asp Thr Leu Glu Thr Thr Cys His Val Leu Asp Pro Thr Pro
                        85                  90                  95

Leu Ala Asn Cys Ser Val Arg Gln Gln Thr Gln His Ala Val Glu Gly
```

```
                100                 105                 110
Asp Cys Asp Ile His Val Leu Lys Gln Asp Gly Gln Phe Ser Val Leu
            115                 120                 125
Phe Thr Lys Cys Asp Ser Ser Pro Asp Ser Ala Glu Asp Val Arg Lys
        130                 135                 140
Leu Cys Pro Asp Cys Pro Leu Leu Ala Pro Leu Asn Asp Ser Arg Val
145                 150                 155                 160
Val His Ala Val Glu Val Ala Leu Ala Thr Phe Asn Ala Glu Ser Asn
                165                 170                 175
Gly Ser Tyr Leu Gln Leu Val Glu Ile Ser Arg Ala Gln Phe Val Pro
            180                 185                 190
Leu Pro Val Ser Val Ser Val Glu Phe Ala Val Ala Ala Thr Asp Cys
        195                 200                 205
Ile Ala Lys Glu Val Val Asp Pro Thr Lys Cys Asn Leu Leu Ala Glu
    210                 215                 220
Lys Gln Tyr Gly Phe Cys Lys Gly Ser Val Ile Gln Lys Ala Leu Gly
225                 230                 235                 240
Gly Glu Asp Val Arg Val Thr Cys Thr Leu Phe Gln Thr Gln Pro Val
                245                 250                 255
Ile Pro Gln Pro Gln Pro Asp Gly Ala Glu Ala Glu Ala Pro Ser Ala
            260                 265                 270
Val Pro Asp Ala Ala Gly Pro Thr Pro Ser Ala Ala Gly Pro Pro Val
        275                 280                 285
Ala Ser Val Val Val Gly Pro Ser Val Val Ala Val Pro Leu Pro Leu
    290                 295                 300
His Arg Ala His Tyr Asp Leu Arg His Thr Phe Ser Gly Val Ala Ser
305                 310                 315                 320
Val Glu Ser Ser Ser Gly Glu Ala Phe His Val Gly Lys Thr Pro Ile
                325                 330                 335
Val Gly Gln Pro Ser Ile Pro Gly Gly Pro Val Arg Leu Cys Pro Gly
            340                 345                 350
Arg Ile Arg Tyr Phe Lys Ile
            355

<210> SEQ ID NO 6
<211> LENGTH: 345
<212> TYPE: PRT
<213> ORGANISM: Mus musculus

<400> SEQUENCE: 6

Met Lys Ser Leu Val Leu Leu Leu Cys Phe Ala Gln Leu Trp Gly Cys
1               5                   10                  15
Gln Ser Ala Pro Gln Gly Thr Gly Leu Gly Phe Arg Glu Leu Ala Cys
            20                  25                  30
Asp Asp Pro Glu Ala Glu Gln Val Ala Leu Leu Ala Val Asp Tyr Leu
        35                  40                  45
Asn Asn His Leu Leu Gln Gly Phe Lys Gln Val Leu Asn Gln Ile Asp
    50                  55                  60
Lys Val Lys Val Trp Ser Arg Arg Pro Phe Gly Val Val Tyr Glu Met
65                  70                  75                  80
Glu Val Asp Thr Leu Glu Thr Cys His Ala Leu Asp Pro Thr Pro
                85                  90                  95
Leu Ala Asn Cys Ser Val Arg Gln Leu Thr Glu His Ala Val Glu Gly
            100                 105                 110
```

-continued

```
Asp Cys Asp Phe His Ile Leu Lys Gln Asp Gly Gln Phe Arg Val Met
        115                 120                 125
His Thr Gln Cys His Ser Thr Pro Asp Ser Ala Glu Asp Val Arg Lys
        130                 135                 140
Leu Cys Pro Arg Cys Pro Leu Leu Thr Pro Phe Asn Asp Thr Asn Val
145                 150                 155                 160
Val His Thr Val Asn Thr Ala Leu Ala Ala Phe Asn Thr Gln Asn Asn
                165                 170                 175
Gly Thr Tyr Phe Lys Leu Val Glu Ile Ser Arg Ala Gln Asn Val Pro
            180                 185                 190
Leu Pro Val Ser Thr Leu Val Glu Phe Val Ile Ala Ala Thr Asp Cys
        195                 200                 205
Thr Ala Lys Glu Val Thr Asp Pro Ala Lys Cys Asn Leu Leu Ala Glu
        210                 215                 220
Lys Gln His Gly Phe Cys Lys Ala Asn Leu Met His Asn Leu Gly Gly
225                 230                 235                 240
Glu Glu Val Ser Val Ala Cys Lys Leu Phe Gln Thr Gln Pro Gln Pro
                245                 250                 255
Ala Asn Ala Asn Ala Val Gly Pro Val Pro Thr Ala Asn Ala Ala Leu
            260                 265                 270
Pro Ala Asp Pro Pro Ala Ser Val Val Val Gly Pro Val Val Val Pro
        275                 280                 285
Arg Gly Leu Ser Asp His Arg Thr Tyr His Asp Leu Arg His Ala Phe
        290                 295                 300
Ser Pro Val Ala Ser Val Glu Ser Ala Ser Gly Glu Thr Leu His Ser
305                 310                 315                 320
Pro Lys Val Gly Gln Pro Gly Ala Ala Gly Pro Val Ser Pro Met Cys
                325                 330                 335
Pro Gly Arg Ile Arg His Phe Lys Ile
            340                 345
```

METHODS AND COMPOSITIONS FOR TREATING, INHIBITING, AND/OR PREVENTING HETEROTOPIC OSSIFICATION

CROSS-REFERENCE TO RELATED PATENT APPLICATIONS

The present application claims the benefit of priority under 35 U.S.C. § 119(e) to U.S. Provisional Application No. 62/887,079, filed on Aug. 15, 2019, the content of which is incorporated herein by reference in its entirety.

STATEMENT REGARDING FEDERALLY SPONSORED RESEARCH OR DEVELOPMENT

This invention was made with government support under AR066539 awarded by the National Institutes of Health. The government has certain rights in the invention.

SEQUENCE LISTING

A Sequence Listing forms part of this application and is submitted as an ASCII text file of the sequence listing named "702581_01807_ST25.txt" which is 19,039 bytes in size and was created on Sep. 9, 2020. The sequence listing is electronically submitted via EFS-Web.

BACKGROUND

The field of the invention relates to methods and compositions for treating, inhibiting, and/or preventing heterotopic ossification in a subject in need thereof. In particular, the field of the invention relates to methods for treating, inhibiting, and/or preventing heterotopic ossification in a subject in need thereof by administering to the subject a therapeutic agent such as an immune checkpoint inhibitor and/or Fetuin-A or a variant thereof. The field of the invention also relates to pharmaceutical compositions and/or pharmaceutical kits comprising an effective amount of an immune checkpoint inhibitor and/or an effective amount of Fetuin-A or a variant thereof for treating, inhibiting, and/or preventing heterotopic ossification in a subject in need thereof.

Heterotopic ossification (HO),[1-3] acquired or hereditary, is characterized by pathological bone formation outside of the normal skeleton, generally following tissue damage. For example, acquired HO (aHO), is commonly triggered by traumatic brain injury, spinal cord injury,[4,5] total hip arthroplasty,[6] wartime trauma, or other traumatic injuries.[4,5,7] Following the acute injury, these patients typically develop persistent low-grade inflammation, chronic pain, unhealed wounds, restricted joint movement, nerve entrapment, and diminished quality of life. Hereditary HO, such as fibrodysplasia ossificans progressiva (FOP),[8] though rare, is much more devastating and life threatening. Notably, even though FOP is caused by gain-of-function mutation of the type 1 bone morphogenetic protein (BMP) receptor,[9,10] ACVR1 (also known as ALK2), the initiation of the HO process in FOP is similarly triggered by abnormal immune responses to minor injuries (also called flare-up) followed by persistent low-grade inflammation.

To model HO in mice, we created a transgenic line (Nse-BMP4) that overexpresses BMP4 under the control of the neuron-specific enolase (Nse) promoter.[11,12] Nse is an important glycolytic enzyme that is modulated by the cellular milieu in response to traumatic injury. In Nse-BMP4 mice, the Nse transgene is induced in macrophages (Mφ) by injury, and the HO that develops in Nse-BMP4 mice is restricted to the site of the injury. The injury-induced local overexpression of BMP4 becomes significant only 3 days post injury (see FIG. 7) indicating that upregulation of BMP signaling is not the initiating event in the subsequent signaling cascade that leads to HO.

In previous studies, we found that both innate immune responses and adaptive immunity play key roles in the pathological process of HO.[11,12] Similarly, recent studies have also shown that disrupted adaptive immune responses are closely associated with HO formation in mice following burn injury and Achilles tenotomy.[13] The overall breadth and magnitude of immune responses are regulated by immune checkpoint proteins (ICs).[14-16] The mammalian genome encodes many different ICs with different expression patterns and functionalities, and some ICs stimulate immune responses to maintain immune homeostasis, whereas others are inhibitory. The central hypothesis of this study is that tissue damage, especially after traumatic injuries,[17-19] induces IC dysregulation leading to a cascade of abnormal immune responses that culminate in HO. This suggests that correcting immune homeostasis using IC inhibitors could be a novel therapeutic approach for prevention and/or treatment of HO.

To test this hypothesis and to explore potential translational applications, we used non-specific immune suppressants including Rapamycin[20] and Ebselen[21] (1) to clarify the role of altered immune homeostasis in HO; (2) substantiated that there is local dysregulation of IC during the HO process; and (3) functionally tested the relationship between IC dysregulation and HO using neutralizing antibodies (Abs) against typical ICs.

Currently, there is no effective treatment for preventing or limiting the extent of HO. Our observations suggest that currently available, Food and Drug Administration (FDA)-approved IC inhibitors may potentially provide a practical therapeutic approach to the disorder.

SUMMARY

The invention relates to methods and compositions for treating, inhibiting, and/or preventing heterotopic ossification in a subject in need thereof. In particular, the intention relates to methods for treating, inhibiting, and/or preventing heterotopic ossification in a subject in need thereof by administering to the subject a therapeutic agent such as an immune checkpoint inhibitor and/or Fetuin-A or a variant thereof. The invention also relates to pharmaceutical compositions and/or pharmaceutical kits comprising an effective amount of an immune checkpoint inhibitor and/or an effective amount of Fetuin-A or a variant thereof for treating, inhibiting, and/or preventing heterotopic ossification in a subject in need thereof.

DETAILED DESCRIPTION

Figure 1:
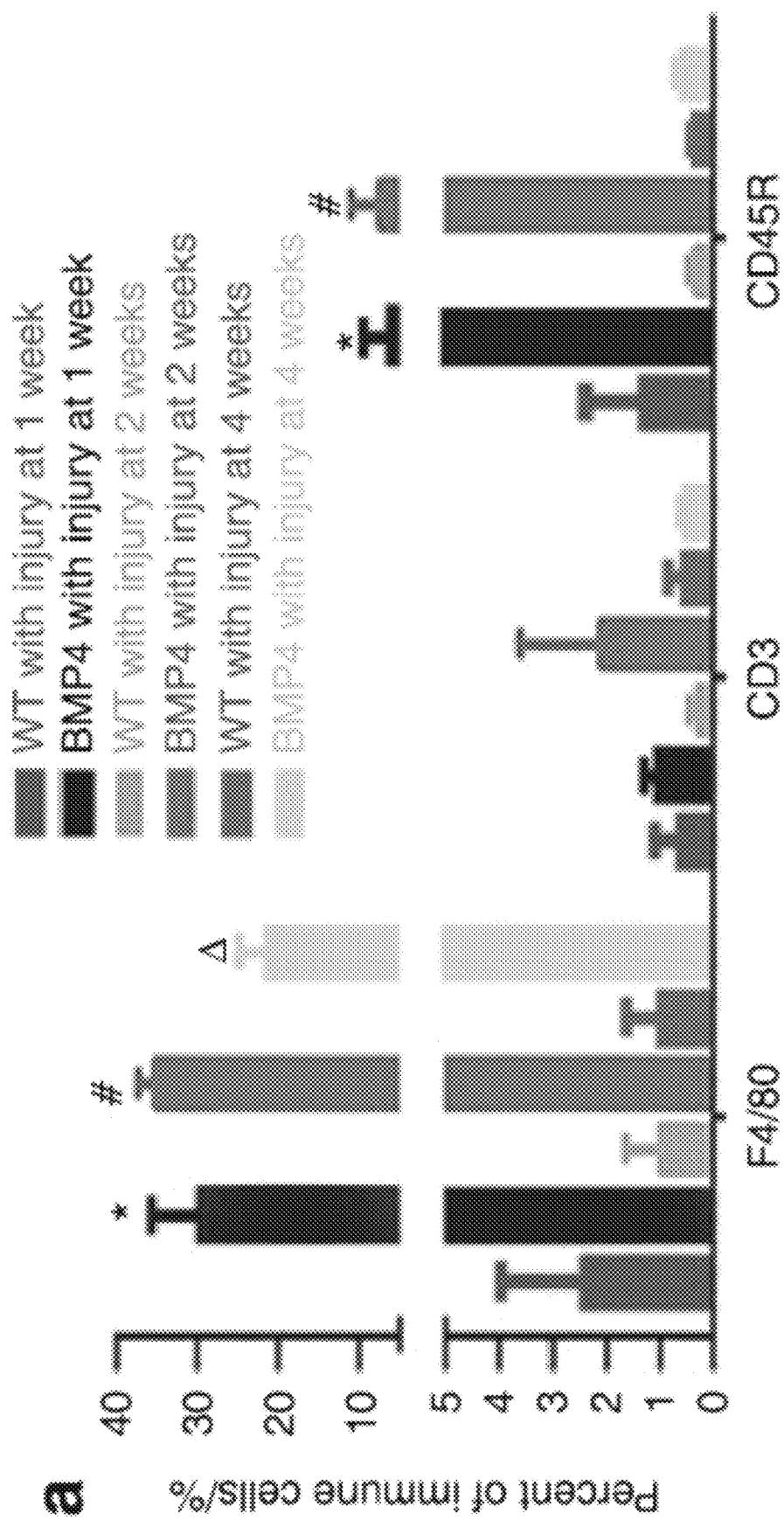
FIG. 1. Evidence of altered immune homeostasis in an HO animal model. a Quantification of local infiltrating immune cells in local lesions in WT and Nse-BMP4 mice at different time points p.i. (n=4 mice per group), *P<0.05 vs group of WT mice with injury at 1 week p.i., #P<0.05 vs group of WT mice with injury at 2 weeks p.i., and ΔP<0.05 vs group of WT mice with injury at 4 weeks p.i. b qRT-PCR results show the expression of pro-inflammatory cytokines (IFN-γ, IL-6, and TNF-α) an anti-inflammatory cytokines (IL-4, IL-10, and IL-13) in the lesions at different time points p.i. (n=5 mice per group), *P<0.05 vs group of WT mice without injury, #P<0.05 vs WT mice with injury. c, d Immunofluorescent images and quantification of Rapamycin- and Ebselen-mediated suppression of WBC infiltration into the lesions at 1, 2, and 4 weeks p.i. (n=4 mice per group), *P<0.05 vs group of WT mice with injury, #P<0.05 vs group of Nse-BMP4 with injury. e-h X-ray imaging revealed that both Rapamycin and Ebselen prevented HO and increased the range of joint motion (i) at the lesion site (n=5 mice per group). White arrows point to HO and joint limitation in the control, *P<0.05 vs control group. Statistics were performed using a repeated-measures ANOVA (a, b, d) or ANOVA (i) with Bonferroni's post hoc test. Scale bar=200 μm.
Figure 1:
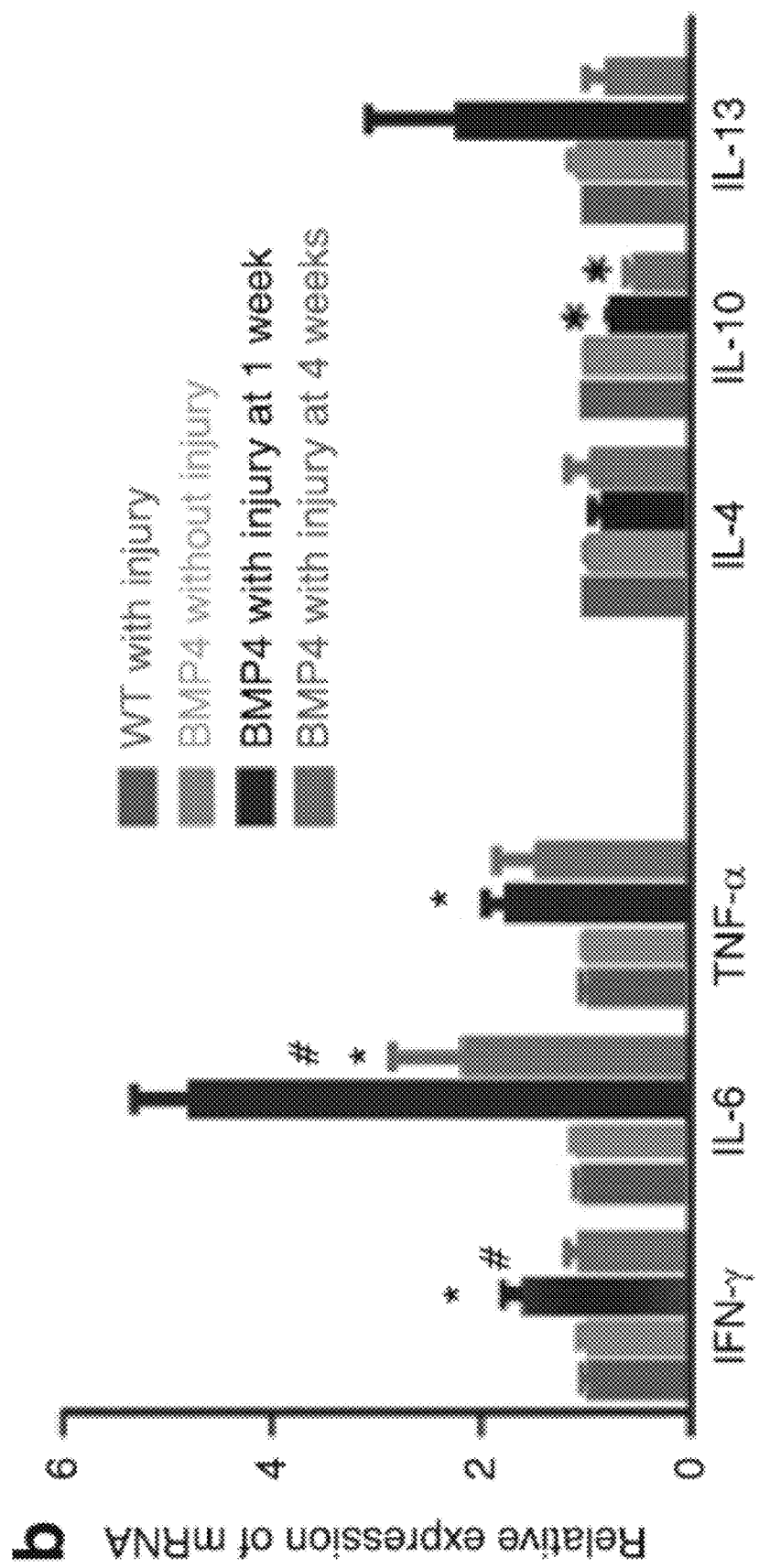
Figure 1:
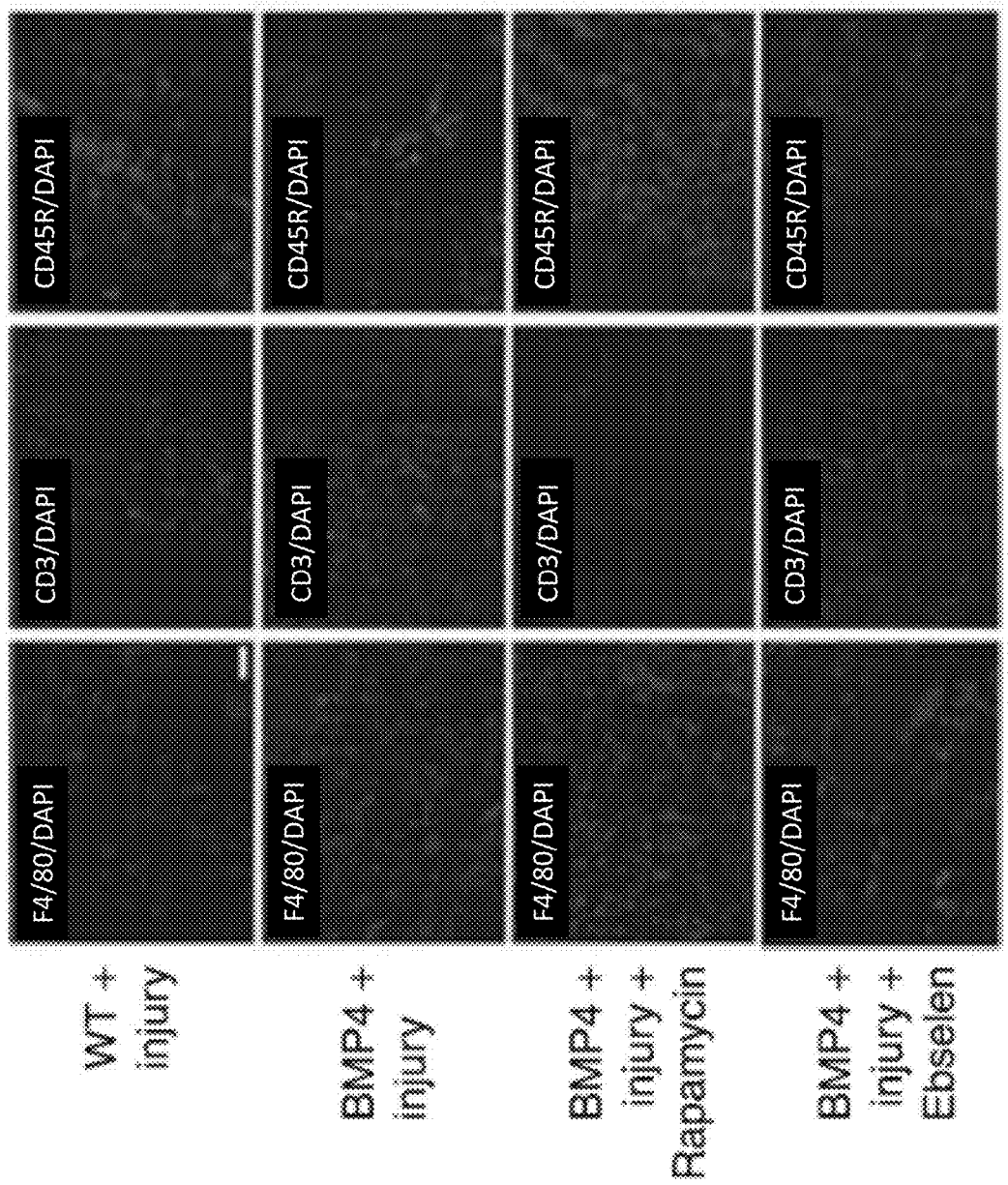
Figure 1:
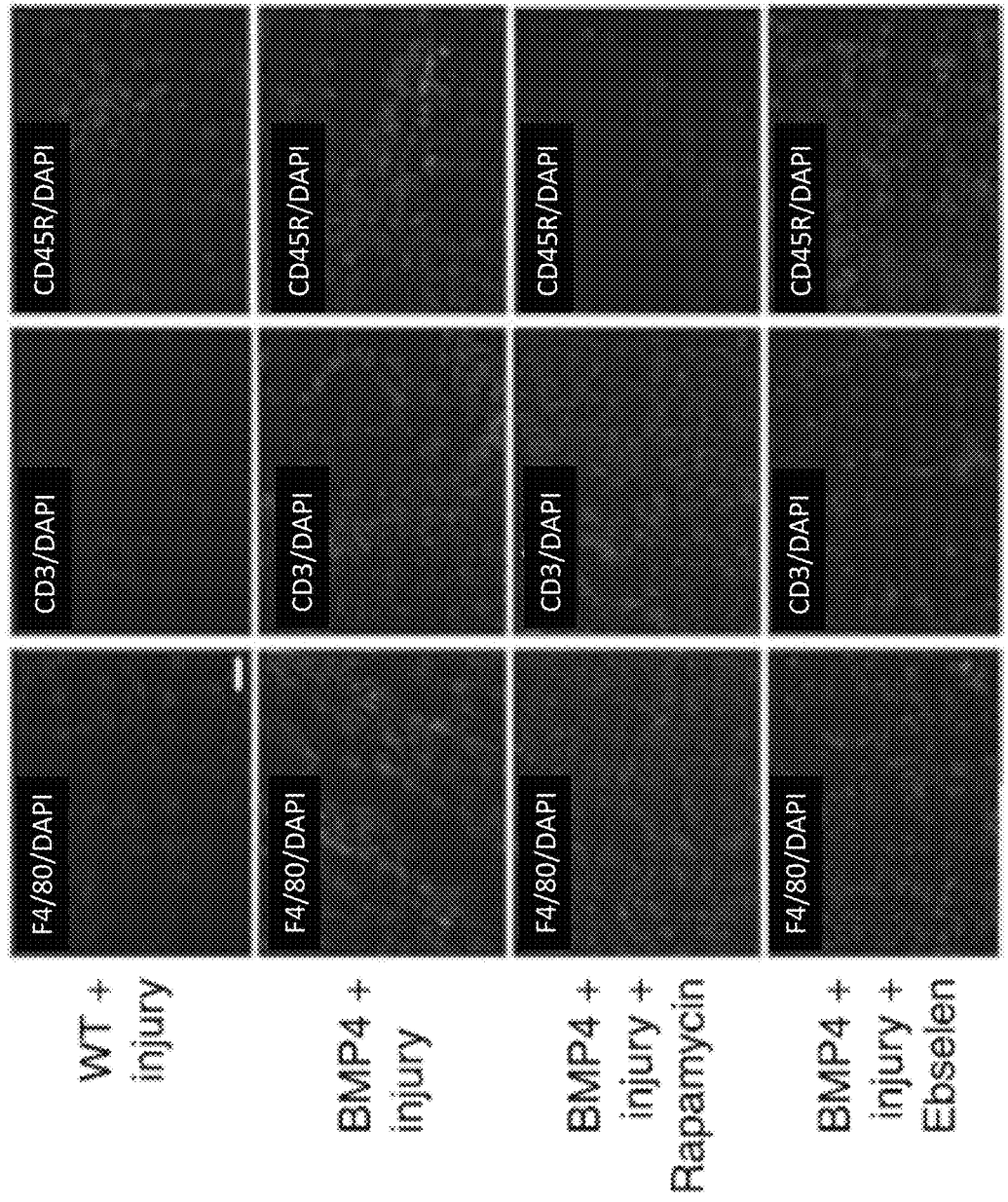
Figure 1:
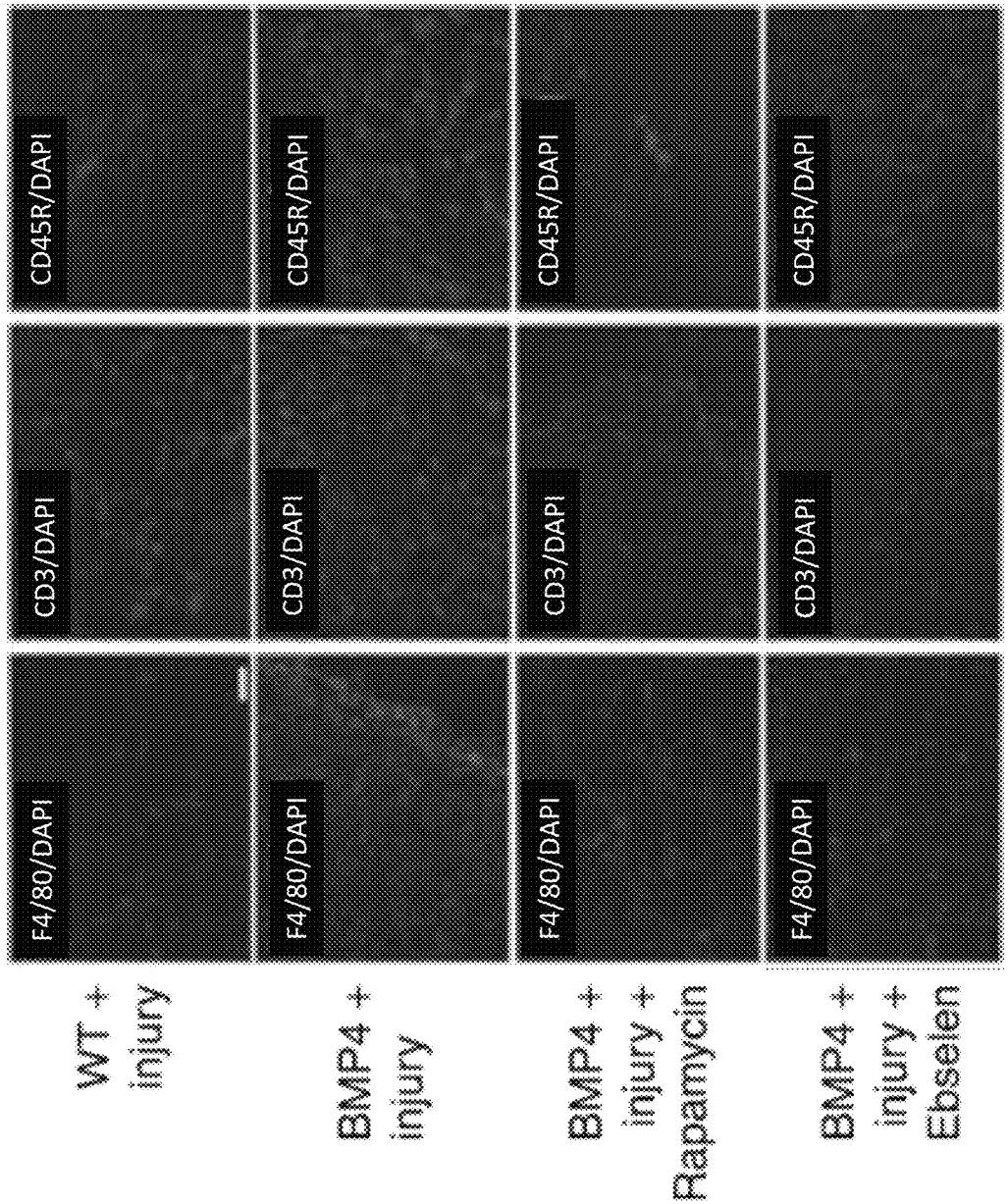
Figure 1:
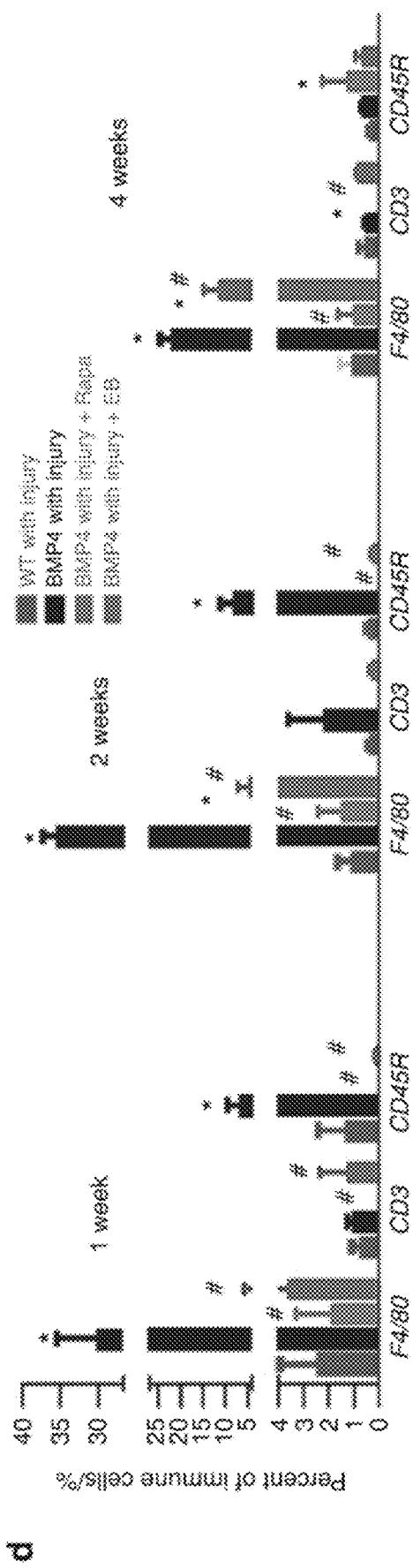
Figure 1:
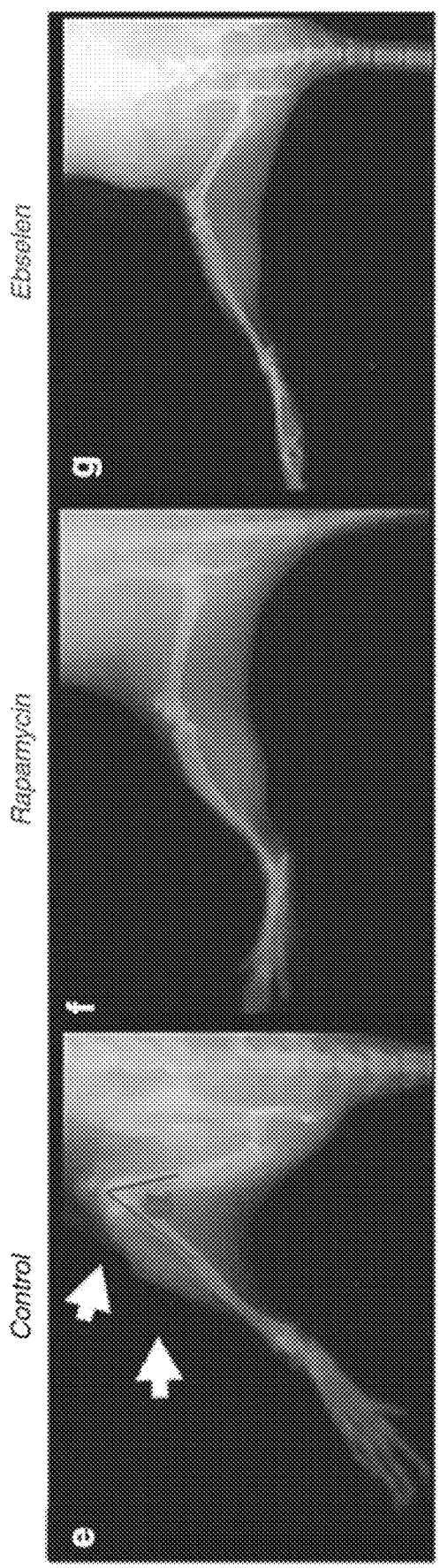
Figure 1:
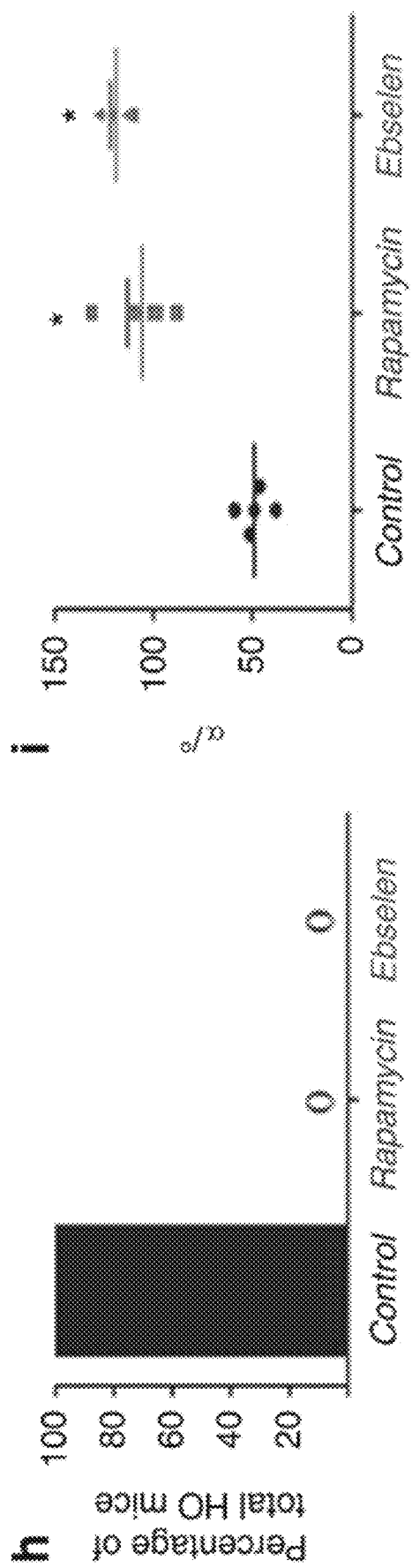

Disclosed are methods and compositions for treating, inhibiting, and/or preventing heterotopic ossification. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human patient.

As used herein, the term "subject" is meant to encompass a person who has heterotopic ossification or is at risk for developing heterotopic ossification. A "subject" may include a subject who has heterotopic ossification or is at risk for developing heterotopic following tissue damage. A "subject" may include a subject who has acquired heterotopic ossification or is at risk for developing heterotopic following tissue damage, which is triggered by traumatic brain injury, spinal cord injury, total hip arthroplasty, wartime trauma and/or other traumatic injuries.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "inhibit" means decreasing or blocking biological activity, for example inhibiting or blocking one or more biological components of an immune checkpoint.

The disclosed methods and compositions relate to treating, inhibiting, and/or preventing heterotopic ossification in a subject in need thereof. In some embodiments, the disclosed methods and compositions relate to treating, inhibiting, and/or preventing heterotopic ossification in a subject in need thereof by administering to the subject a therapeutic agent that comprises an immune checkpoint inhibitor or blocker.

As such, the disclosed methods may utilize and/or the disclosed composition may comprise one or more immune checkpoint inhibitors or blockers. Immune checkpoint inhibitors and blockers are known in the art. In some embodiments, the immune checkpoint inhibitor or blocker of the disclosed methods and composition is selected from the group consisting of, but not limited to, an anti CD152 antibody (i.e., an CTLA-4 antibody) (e.g., Ipilimumab or Tremelimumab), an anti PD-1 antibody (MDX-1106, BMS-936558, MK3475, CT-011, AMP-224), an anti PD-L1 antibody (e.g., MDX-1105), an anti IDO-1 antibody, an anti IDO-2 antibody, an anti KIR antibody, an anti CD70 antibody, an anti LAG-3 antibody (e.g., IMP321), an anti B7-H3 antibody (e.g., MGA271), an anti B7-H4 antibody, an anti TIM3 antibody, and combinations thereof.

In some embodiments, the disclosed methods and compositions relate to treating and/or inhibiting heterotopic ossification in a subject in need thereof by administering to the subject a therapeutic agent that comprises Fetuin A. Fetuin A may alternatively be referred to as alpha-2-HS glycoprotein. Four human isoforms of Fetuin A are known and are expressed as preproteins which are processed to produce the mature isoforms:

```
Isoform 1 preprotein (SEQ ID NO: 1);
  1 mksivlllcl aqlwgchsap hgpgliyrqp ncddpeteea alvaidyinq nlpwgykhtl 61 nqidevkvwp qqpsgelfei eidtlettch vldptpvarc svrqlkehav egdcdfqllk
```

```
-continued
121 ldgkfsvvya kcdsspadsa edvrkvcqdc pllaplndtr vvhaakaala afnaqnngsn 181 fqleeisraq lvplppstyv eftvsgtdcv akeateaakc nllaekqygf ckatlseklg 241 gaevavtcmv fqtqpvssqp qpeganeavp tpvvdpdapp spplgapglp pagsppdshv 301 llaappghql hrahydlrht fmgvvslgsp sgevshprkt rtvvqpsvga aagpvvppcp 361 grirhfkv Isoform 2 preprotein (SEQ ID NO: 2)
  1 mkslvlllcl aqlwgchsap hgpgliyrqp ncddpeteea alvaidyinq nlpwgykhtl 61 nqidevkvwp qqpsgelfei eidtlettch vldptpvarc svrqlkehav egdcdfqllk 121 ldgkfsvvya kcdsspdsae dvrkvcqdcp llaplndtrv vhaakaalaa fnaqnngsnf 181 qleeisraql vplppstyve ftvsgtdcva keateaakcn llaekqygfc katlseklgg 241 aevavtcmvf qtqpvssqpq peganeavpt pvvdpdapps pplgapglpp agsppdshvl 301 laappghqlh rahydlrhtf mgvvslgsps gevshprktr tvvqpsvgaa agpvvppcpg 361 rirhfkv Isoform 3 preprotein (SEQ ID NO: 3)
  1 mkslvlllcl aqlwgchsap hgpgliyrqp ncddpeteea alvaidyinq nlpwgykhtl 61 nqidevkvwp qpsgelfeie idtlettchv ldptpvarcs vrqlkehave gdcdfqllkl 121 dgkfsvvyak cdsspdsaed vrkvcqdcpl laplndtrvv haakaalaaf naqnngsnfq 181 leeisraqlv plppstyvef tvsgtdcvak eateaakcnl laekqygfck atlseklgga 241 evavtcmvfq tqpvssqpqp eganeavptv vvdpdappsp plgapglppa gsppdshvll 301 aappghqlhr ahydlrhtfm gvvslgspsg evshprktrt vvqpsvgaaa gpvvppcpgr 361 irhfkv Isoform 4 preprotein (SEQ ID NO: 4)
  1 mkslvlllcl aqlwgchsap hgpgliyrqp ncddpeteea alvaidyinq nlpwgykhtl 61 nqidevkvwp qqpsgelfei eidtlettch vldptpvarc svrqlkehav egdcdfqllk 121 ldgkfsvvya kcdsspdsae dvrkvcqdcp llaplndtrv vhaakaalaa fnaqnngsnf 181 qleeisraql vplppstyve ftvsgtdcva keateaakcn llaekpvssq pqpeganeav 241 ptpvvdpdap pspplgapgl ppagsppdsh vllaappghq lhrahydlrh tfmgvvslgs 301 psgevshprk trtvvqpsvg aaagpvvppc pgrirhfkv
```

The disclosed methods may utilize and the disclosed compositions may comprise any suitable isoform of Fetuin A, optionally in its full-length or processed form, for example, in which amino acids 1-18 are removed from the preprotein. The disclosed method may utilize and the disclosed compositions may comprise variant forms of Fetuin A, for example a variant having at least about 80%, 85%, 90%, 95%, 96%, 97%, 98%, or 99% sequence identity to any of full-length SEQ ID NOs:1-3, which variant may include a fragment having at least about 80%, 85%, 90%, 95%, 96%, 97%, 98%, or 99% sequence identity to any of full-length SEQ ID NOs:1-3. Methods and algorithms for determining sequence identity are available at public databases including the database for the National Center for Biotechnology Information (NCBI) of the National Institutes of Health (NIH), and its Basic Local Alignment Search Tool (BLAST). Optionally, the Fetuin-A variants exhibit one or more biological activities of wild-type Fetuin-A. Optionally, the Fetuin-A and variants of Fetuin A administered in the disclosed methods and present in the disclosed compositions may function to bind, carry, and transport free fatty acids in circulation of a subject that has been administered the Fetuin-A or variants thereof.

ILLUSTRATED EMBODIMENTS

The following Embodiments are illustrative and should not be interpreted to limit the scope of the claimed subject matter.

Embodiment 1. A method for treating, inhibiting, and/or preventing heterotopic ossification in a subject in need thereof, the method comprising administering to the subject an effective amount of an immune checkpoint inhibitor to treat, inhibit, and/or prevent heterotopic ossification in the subject.

Embodiment 2. The method of embodiment 1, wherein the subject has experienced traumatic injury prior to administering to the subject the effective amount of the immune checkpoint inhibitor to treat, inhibit, and/or prevent heterotopic ossification in the subject.

Embodiment 3. The method of embodiment 1, wherein the subject has undergone surgery prior to administering to the subject the effective amount of the immune checkpoint inhibitor to treat, inhibit, and/or prevent heterotopic ossification in the subject.

Embodiment 4. The method of any of the foregoing embodiments, wherein the immune checkpoint inhibitor is selected from the group consisting of an anti CD152 (i.e., an anti CTLA-4 antibody) (e.g., Ipilimumab or Tremelimumab), an anti PD-1 antibody (MDX-1106, BMS-936558, MK3475, CT-011, AMP-224), an anti PD-L1 antibody (e.g., MDX-1105), an anti IDO-1 antibody, an anti IDO-2 antibody, an anti KIR antibody, an anti CD70 antibody, an anti LAG-3 antibody (e.g., IMP321), an anti B7-H3 antibody (e.g., MGA271), an anti B7-H4 antibody, an anti TIM3 antibody, and combinations thereof.

Embodiment 5. The method of any of the foregoing embodiments, wherein the immune checkpoint inhibitor is an anti CD152 antibody (i.e., an anti CTLA-4 antibody).

Embodiment 6. The method of any of the foregoing embodiments, wherein the immune checkpoint inhibitor is an anti PD-1 antibody.

Embodiment 7. The method of any of the foregoing embodiments, wherein the immune checkpoint inhibitor is an anti PD-L1 antibody.

Embodiment 8. A method for treating, inhibiting, and/or preventing heterotopic ossification in a subject in need thereof, the method comprising administering to the subject an effective amount of Fetuin-A or a variant thereof to treat, inhibit, and/or prevent heterotopic ossification in the subject.

Embodiment 9. The method of embodiment 8, wherein the subject has experienced traumatic injury prior to administering to the subject the effective amount of the Fetuin-A or the variant thereof to treat, inhibit, and/or prevent heterotopic ossification in the subject.

Embodiment 10. The method of embodiment 8, wherein the subject has undergone surgery prior to administering to the subject the effective amount of the Fetuin-A or the variant thereof to treat, inhibit, and/or prevent heterotopic ossification in the subject.

Embodiment 11. The method of any of embodiments 8-10, wherein the Fetuin-A or the variant thereof comprises an amino acid sequence of any of SEQ ID NOs:1-4, a processed form of any of SEQ ID NOs:1-4 lacking amino acids 1-18, or a variant of any of SEQ ID NOs:1-4 or a processed form of any of SEQ ID NOs:1-4 lacking amino acids 1-18, wherein the variant has at least about 80% sequence identity to any of SEQ ID NOs:1-4 or a processed form of any of SEQ ID NOs:1-4 lacking amino acids 1-18.

Embodiment 12. A method for treating, inhibiting, and/or preventing heterotopic ossification in a subject in need thereof, the method comprising: (i) administering to the subject an effective amount of an immune checkpoint inhibitor to treat, inhibit, and/or prevent heterotopic ossification in the subject; and (ii) administering to the subject an effective amount of Fetuin-A or a variant thereof to treat, inhibit, and/or prevent heterotopic ossification in the subject, wherein the effective amount of the immune checkpoint inhibitor is administered to the subject before, concurrently with, or after the effective amount of the Fetuin-A is administered to the subject.

Embodiment 13. The method of embodiment 12, wherein the subject has experienced traumatic injury prior to administering to the subject the effective amount of the immune checkpoint inhibitor to treat, inhibit, and/or prevent heterotopic ossification in the subject; and/or wherein the subject has experienced traumatic injury prior to administering to the subject the effective amount of the Fetuin-A or the variant thereof to treat, inhibit, and/or prevent heterotopic ossification in the subject.

Embodiment 14. The method of embodiment 12, wherein the subject has undergone surgery prior to administering to the subject the effective amount of the immune checkpoint inhibitor to treat, inhibit, and/or prevent heterotopic ossification in the subject; and/or wherein the subject has undergone surgery prior to administering to the subject the effective amount of the Fetuin-A or the variant thereof to treat, inhibit, and/or prevent heterotopic ossification in the subject.

Embodiment 15. The method of any of embodiments 12-14, wherein the immune checkpoint inhibitor is selected from the group consisting of an anti CD152 (i.e., an anti CTLA-4 antibody) (e.g., Ipilimumab or Tremelimumab), an anti PD-1 antibody (MDX-1106, BMS-936558, MK3475, CT-011, AMP-224), an anti PD-L1 antibody (e.g., MDX-1105), an anti IDO-1 antibody, an anti IDO-2 antibody, an anti KIR antibody, an anti CD70 antibody, an anti LAG-3 antibody (e.g., IMP321), an anti B7-H3 antibody (e.g., MGA271), an anti B7-H4 antibody, an anti TIM3 antibody, and combinations thereof.

Embodiment 16. The method of any of embodiments 12-15, wherein the immune checkpoint inhibitor is an anti CD152 antibody (i.e., an anti CTLA-4 antibody).

Embodiment 17. The method of any of embodiments 12-15, wherein the immune checkpoint inhibitor is an anti PD-1 antibody.

Embodiment 18. The method of any of embodiments 12-15, wherein the immune checkpoint inhibitor is an anti PD-L1 antibody.

Embodiment 19. The method of any of embodiments 12-18, wherein the Fetuin-A or the variant thereof comprises an amino acid sequence of any of SEQ ID NOs:1-4, a processed form of any of SEQ ID NOs:1-4 lacking amino acids 1-18, or a variant of any of SEQ ID NOs:1-4 or a processed form of any of SEQ ID NOs:1-4 lacking amino acids 1-18, wherein the variant has at least about 80% sequence identity to any of SEQ ID NOs:1-4 or a processed form of any of SEQ ID NOs:1-4 lacking amino acids 1-18.

Embodiment 20. A pharmaceutical composition for treating, inhibiting, and/or preventing heterotopic ossification in a subject in need thereof, the pharmaceutical composition comprising: (i) an effective amount of an immune checkpoint inhibitor to treat, inhibit, and/or prevent heterotopic ossification in the subject; and (ii) a pharmaceutical carrier.

Embodiment 21. The pharmaceutical composition of embodiment 20, wherein the immune checkpoint inhibitor is selected from the group consisting of an anti CD152 (i.e., an anti CTLA-4 antibody) (e.g., Ipilimumab or Tremelimumab), an anti PD-1 antibody (MDX-1106, BMS-936558, MK3475, CT-011, AMP-224), an anti PD-L1 antibody (e.g., MDX-1105), an anti IDO-1 antibody, an anti IDO-2 antibody, an anti KIR antibody, an anti CD70 antibody, an anti LAG-3 antibody (e.g., IMP321), an anti B7-H3 antibody (e.g., MGA271), an anti B7-H4 antibody, an anti TIM3 antibody, and combinations thereof.

Embodiment 22. The pharmaceutical composition of embodiment 20 or 21, wherein the immune checkpoint inhibitor is an anti CD152 antibody (i.e., an anti CTLA-4 antibody).

Embodiment 23. The pharmaceutical composition of embodiment 20 or 21, wherein the immune checkpoint inhibitor is an anti PD-1 antibody.

Embodiment 24. The pharmaceutical composition of embodiment 20 or 21, wherein the immune checkpoint inhibitor is an anti PD-L1 antibody.

Embodiment 25. A pharmaceutical composition for treating, inhibiting, and/or preventing heterotopic ossification in a subject in need thereof, the pharmaceutical composition comprising: (i) an effective amount of Fetuin-A or the variant thereof to treat, inhibit, and/or prevent heterotopic ossification in the subject; and (ii) a pharmaceutical carrier.

Embodiment 26. The pharmaceutical composition of embodiment 25, wherein the Fetuin-A or the variant thereof comprises an amino acid sequence of any of SEQ ID NOs:1-4, a processed form of any of SEQ ID NOs:1-4 lacking amino acids 1-18, or a variant of any of SEQ ID NOs:1-4 or a processed form of any of SEQ ID NOs:1-4 lacking amino acids 1-18, wherein the variant has at least about 80% sequence identity to any of SEQ ID NOs:1-4 or a processed form of any of SEQ ID NOs:1-4 lacking amino acids 1-18.

Embodiment 27. A pharmaceutical kit for treating, inhibiting, and/or preventing heterotopic ossification in a subject in need thereof, the pharmaceutical kit comprising: (i) an effective amount of an immune checkpoint inhibitor to treat, inhibit, and/or prevent heterotopic ossification in the subject; and (ii) an effective amount of Fetuin-A or a variant thereof to treat, inhibit, and/or prevent heterotopic ossification in the subject.

Embodiment 28. The pharmaceutical kit of embodiment 27, wherein the immune checkpoint inhibitor is selected from the group consisting of an anti CD152 (i.e., an anti CTLA-4 antibody) (e.g., Ipilimumab or Tremelimumab), an anti PD-1 antibody (MDX-1106, BMS-936558, MK3475, CT-011, AMP-224), an anti PD-L1 antibody (e.g., MDX-1105), an anti IDO-1 antibody, an anti IDO-2 antibody, an anti KIR antibody, an anti CD70 antibody, an anti LAG-3 antibody (e.g., IMP321), an anti B7-H3 antibody (e.g., MGA271), an anti B7-H4 antibody, an anti TIM3 antibody, and combinations thereof.

Embodiment 29. The pharmaceutical kit of embodiment 27 or 28, wherein the immune checkpoint inhibitor is an anti CD152 antibody (i.e., an anti CTLA-4 antibody).

Embodiment 30. The pharmaceutical kit of embodiment 27 or 28, wherein the immune checkpoint inhibitor is an anti PD-1 antibody.

Embodiment 31. The pharmaceutical kit of embodiment 27 or 28, wherein the immune checkpoint inhibitor is an anti PD-L1 antibody.

Embodiment 32. The pharmaceutical kit of any of embodiments 27-31, wherein the Fetuin-A or the variant thereof comprises an amino acid sequence of any of SEQ ID NOs:1-4, a processed form of any of SEQ ID NOs:1-4 lacking amino acids 1-18, or a variant of any of SEQ ID NOs:1-4 or a processed form of any of SEQ ID NOs:1-4 lacking amino acids 1-18, wherein the variant has at least about 80% sequence identity to any of SEQ ID NOs:1-4 or a processed form of any of SEQ ID NOs:1-4 lacking amino acids 1-18.

EXAMPLES

The following Examples are illustrative and should not be interpreted to limit the scope of the claimed subject matter.

Example 1—Inhibition of Immune Checkpoints Prevents Injury-Induced Heterotopic Ossification Reference is made to Kan et al., "Inhibition of immune checkpoints prevents injury-induced heterotopic ossification," Bone Res. 2019; 7; 33; pages 1-8, published online Nov. 1, 2019, the content of which is incorporated herein by reference in its entirety.

Abstract

Heterotopic ossification (HO), true bone formation in soft tissue, is closely associated with abnormal injury/immune responses. We hypothesized that a key underlying mechanism of HO might be injury-induced dysregulation of immune checkpoint proteins (ICs). We found that the earliest stages of HO are characterized by enhanced infiltration of polarized macrophages into sites of minor injuries in an animal model of HO. The non-specific immune suppressants, Rapamycin and Ebselen, prevented HO providing evidence of the central role of the immune responses. We examined the expression pattern of ICs and found that they are dysregulated in HO lesions. More importantly, loss of function of inhibitory ICs (including PD1, PD-L1, and CD152) markedly inhibited HO, whereas loss of function of stimulatory ICs (including CD40L and OX-40L) facilitated HO. These findings suggest that IC inhibitors may provide a therapeutic approach to prevent or limit the extent of HO.

Applications

Applications of the disclosed technology may include, but are not limited to: (i) inhibition of heterotopic ossification (HO) in early stages of a subject having HO or at risk for developing HO; and (ii) prevention of potential HO formation that is induced by traumatic injury or surgery intraoperatively or post-operatively, as a prophylaxis, for example, in a medical institution environment.

Advantages

Advantages of the disclosed technology may include, but are not limited to: (i) the disclosed methods and compositions utilize immune checkpoint inhibitors or blockers which are mechanism-specific and are approved by the Food and Drug Administration (FDA).

Description

The inventors have used a CTLA-4/CD152 blocker and a PD-1/PD-L1 blocker to inhibit heterotopic ossification (HO) that has been induced by traumatic injury and to correct an abnormal injury response. The CTLA-4/CD152 blocker and a PD-1/PD-L1 blocker utilized by the present invention were first described for use in cancer immunotherapy.

Results

Evidence of altered immune homeostasis in an HO animal model. The Nse-BMP4 transgenic mouse recapitulates the hallmarks of both aHO and FOP (refs. [11,12,22-25] and FIG. 7). We examined the infiltration of immune cells into sites of minor injury and the production of cytokines in Nse-BMP4 and wild-type (WT) mice and in uninjured controls at different time points post-injury (p.i.). Infiltration into the injury sites of Mϕ/monocytes (F4/80), T cells (CD3), and B cells (CD45R) was examined by immunohistochemistry, and responses to the same injury differed significantly in Nse-BMP4 and WT mice (FIG. 1a, c). All tested immune cells were found in the HO lesions. The distribution patterns varied greatly for different subpopulations of cells at different time points, but Mϕ were the predominant infiltrating immune cells throughout the entire HO process. We also measured the expression of inflammatory cytokines in the lesion sites using quantitative real-time reverse transcription polymerase chain reaction (qRT-PCR) and found that all the tested cytokines were dysregulated. The pro-inflammatory cytokines, interferon (IFN)-γ and tumor necrosis factor (TNF)-α, were transiently increased at 1 week p.i., but were decreased at 4 weeks p.i. in Nse-BMP4 mice (FIG. 1b). In contrast, the opposite trend was observed for the anti-inflammatory cytokine, interleukin (IL)-10.

Figure 8:
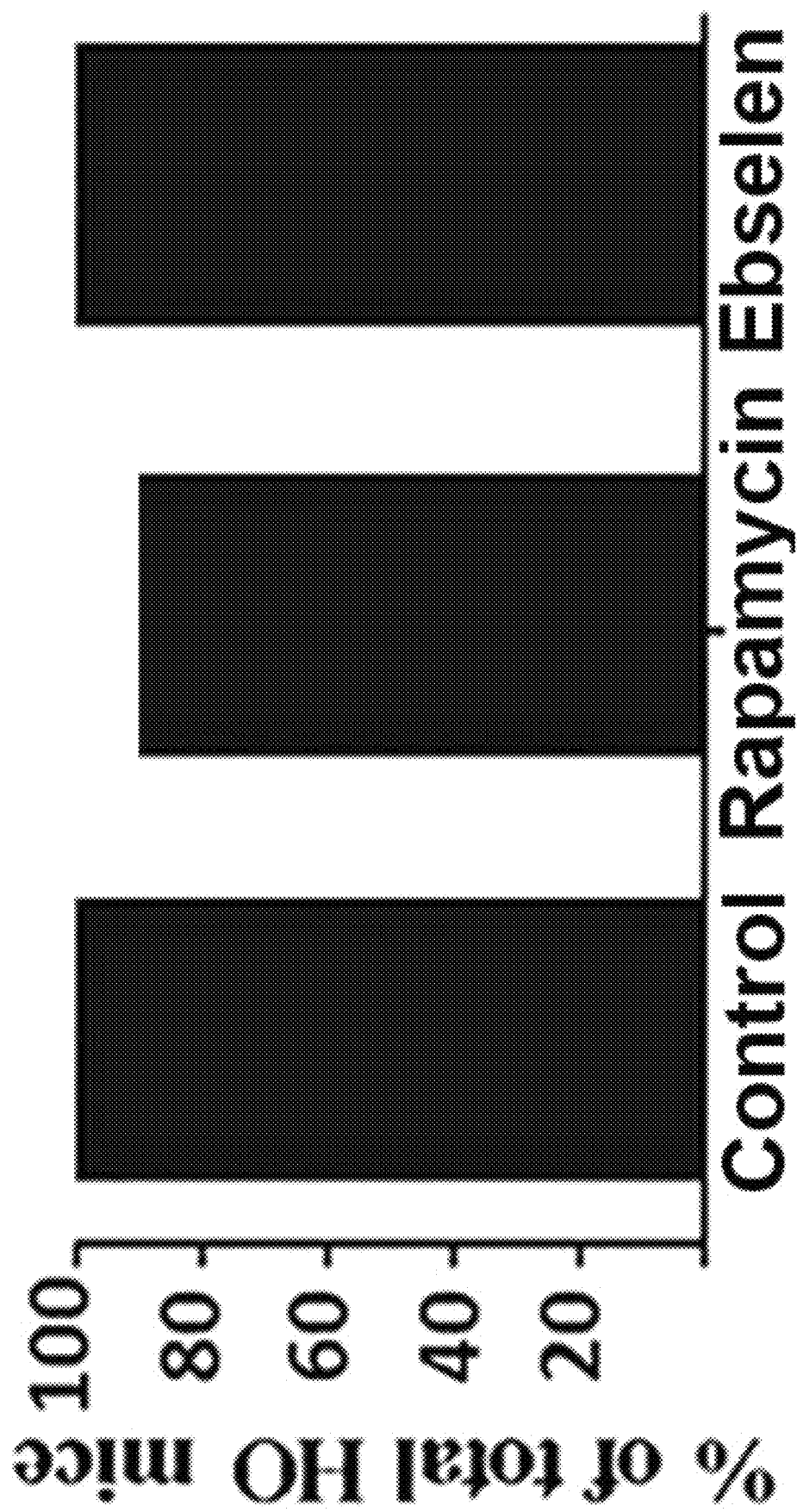
FIG. 8. Ebselen and Rapamycin fail to block HO when treatment is delayed until day 10. Treatment with Ebselen or Rapamycin was delayed until day 10 and then given in the same dosages as in FIG. 1. Nine of ten mice treated with Rapamycin developed HO and all 10 mice treated with Ebselen developed HO.

Non-specific immune suppressors, Rapamycin and Ebselen, inhibit HO. We next tested the causal relationship between the altered immune responses and the subsequent HO. We repeated the injury procedure and then treated the mice with Rapamycin or Ebselen, for 2 weeks. Rapamycin and Ebselen each inhibited local immune cell infiltration (FIG. 1c, d). X-ray imaging revealed that Rapamycin and Ebselen also each inhibited HO formation (FIG. 1e-h) and increased the range of joint motion at the injury site (FIG. 1i). Rapamycin and Ebselen were effective in preventing HO when treatment was initiated any time during the first 10 days after the injury. Treatment started after the first 10 days no longer altered the progression of HO (FIG. 8). Other than inhibition of HO formation, no effects on bone were noted for either Rapamycin or Ebselen either radiographically or histopathologically.

Figure 2:
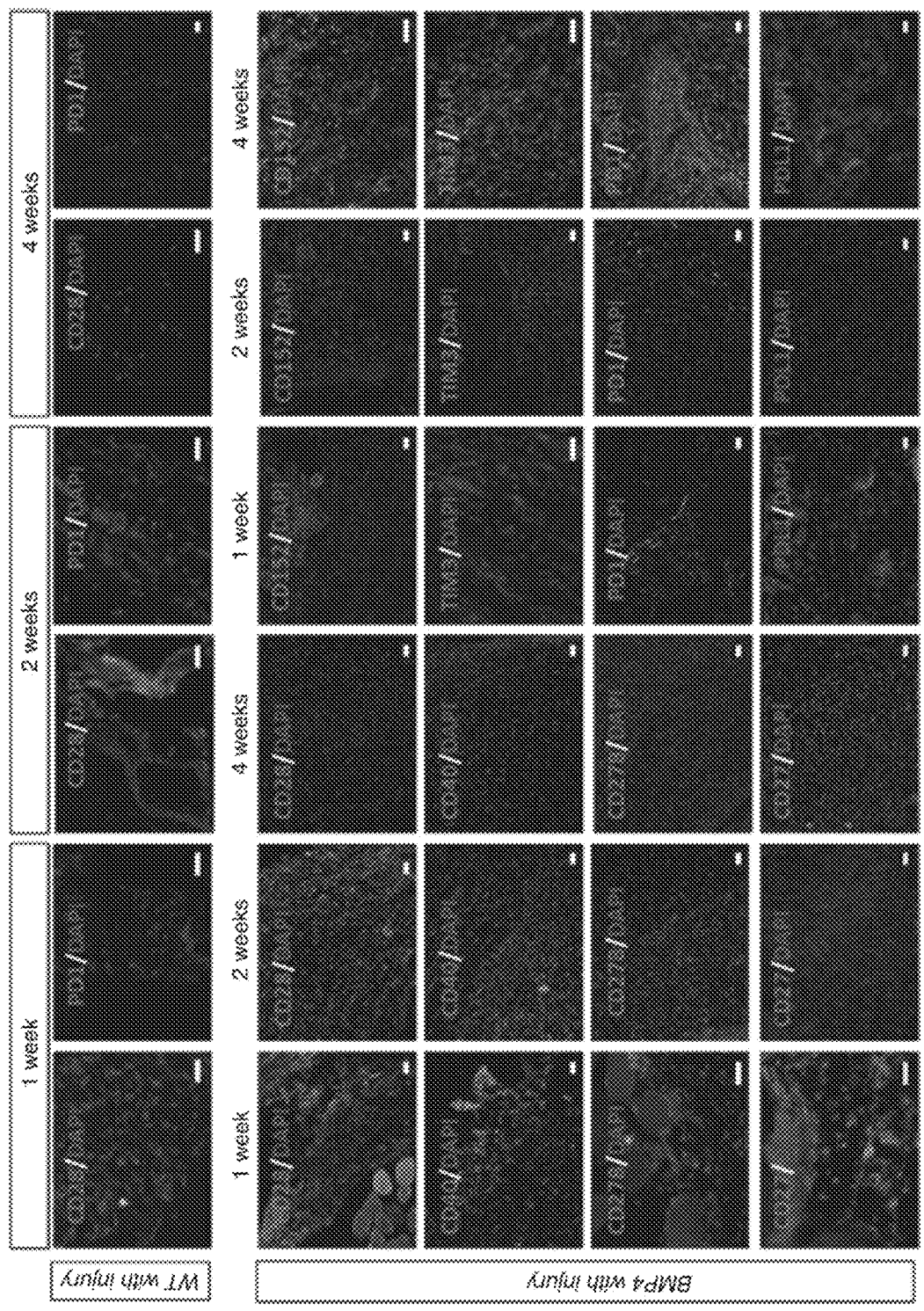
FIG. 2. Immune checkpoint proteins are dynamically dysregulated in HO lesions. a Immunofluorescence staining showed the expression of CD28 and PD1 in WT mice at 1, 2 and 4 weeks p.i. In Nse-BMP4 mice, immunostaining revealed a distinct expression pattern of stimulatory ICs (CD27, CD28, CD40, CD278) in HO lesions at 1, 2, and 4 weeks p.i. b-d Quantitation of the percentages of cells expressing IC proteins in Wt and Nse-BMP4 mice at 1, 2, and 4 weeks p.i. (n=4 per group per time point). In WT mice with injury, the percentages of cells expressing ICs were generally low. In contrast, in Nse-BMP4 mice, the stimulatory ICs, including CD27, CD28, CD278, and CD40, and inhibitory ICs, including Tim3, CD152, PD1, and PD-L1, were differentially dysregulated. Note that stimulatory ICs generally were abnormally increased at early stages and then decreased, while some inhibitory ICs remained increased at late stages. *P<0.02 compared to wild-type control at all time points. #P<0.05 compared to 1 week time point in the Nse-BMP4 group. Statistics were performed using a repeated-measures ANOVA with Bonferroni's post hoc test. Scale bar=200 μm.
Figure 2:
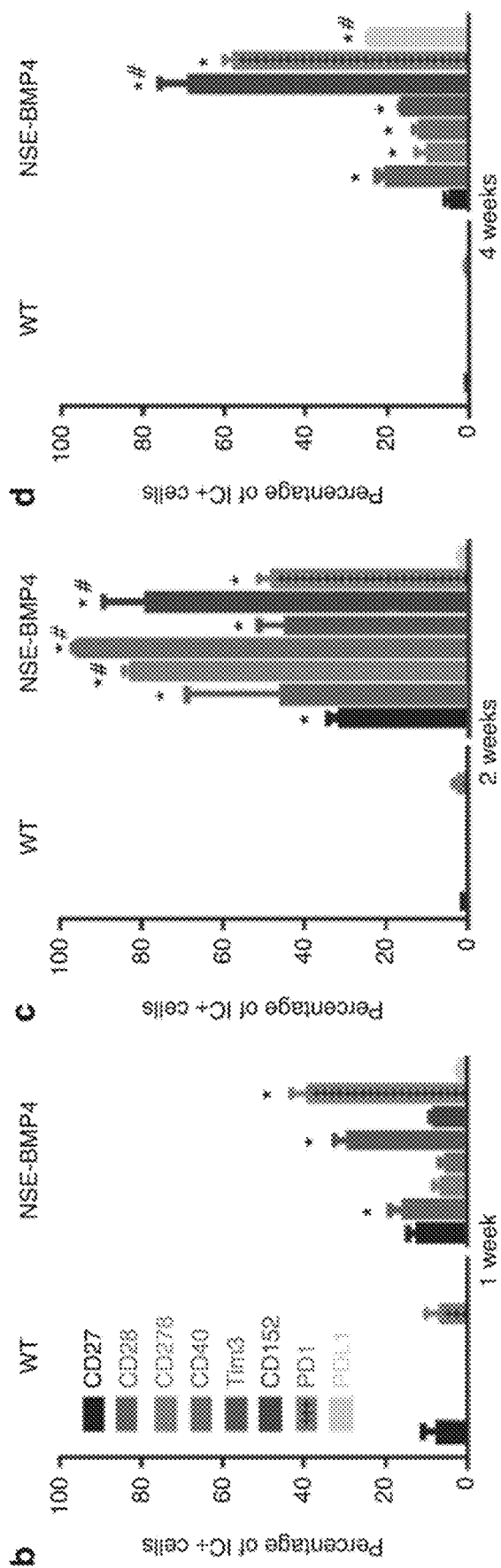
Figure 3:
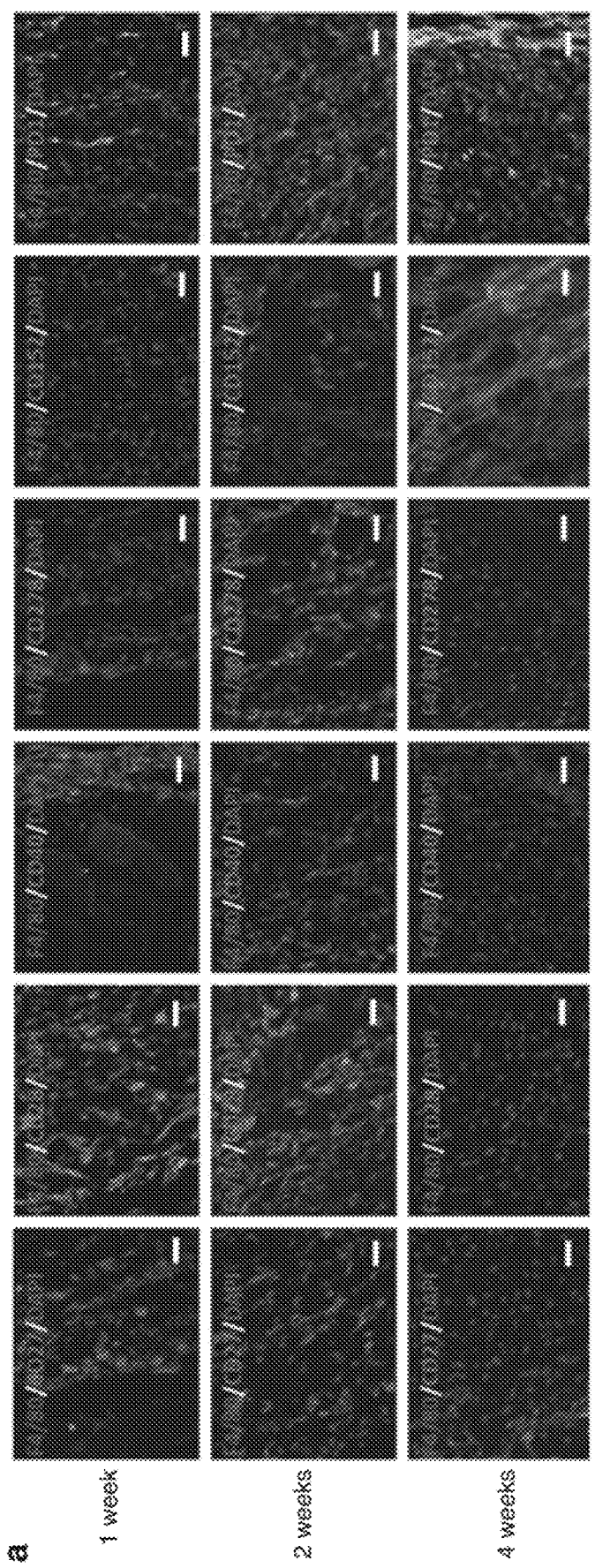
FIG. 3. Immune checkpoint proteins were extensively co-localized within macrophages. a Immunostaining showed the co-localization of F4/80 and ICs at 1, 2, and 4 weeks p.i. b Double-staining of ICs with F4/80 found that, within the macrophage population, stimulatory and inhibitory IC+ cells followed similar respective patterns (n=4). Scale bar in all panels=200 μm *Differs from 1- and 2-week groups at P<0.05; **Differs from 1- and 2-week groups at P<0.01; &Differs from 1-week group at P<0.05; #Differs from the 2-week group at P<0.05. Statistics were performed using a repeated-measures ANOVA with Bonferroni's post hoc test. Scale bar=200 μm.
Figure 3:
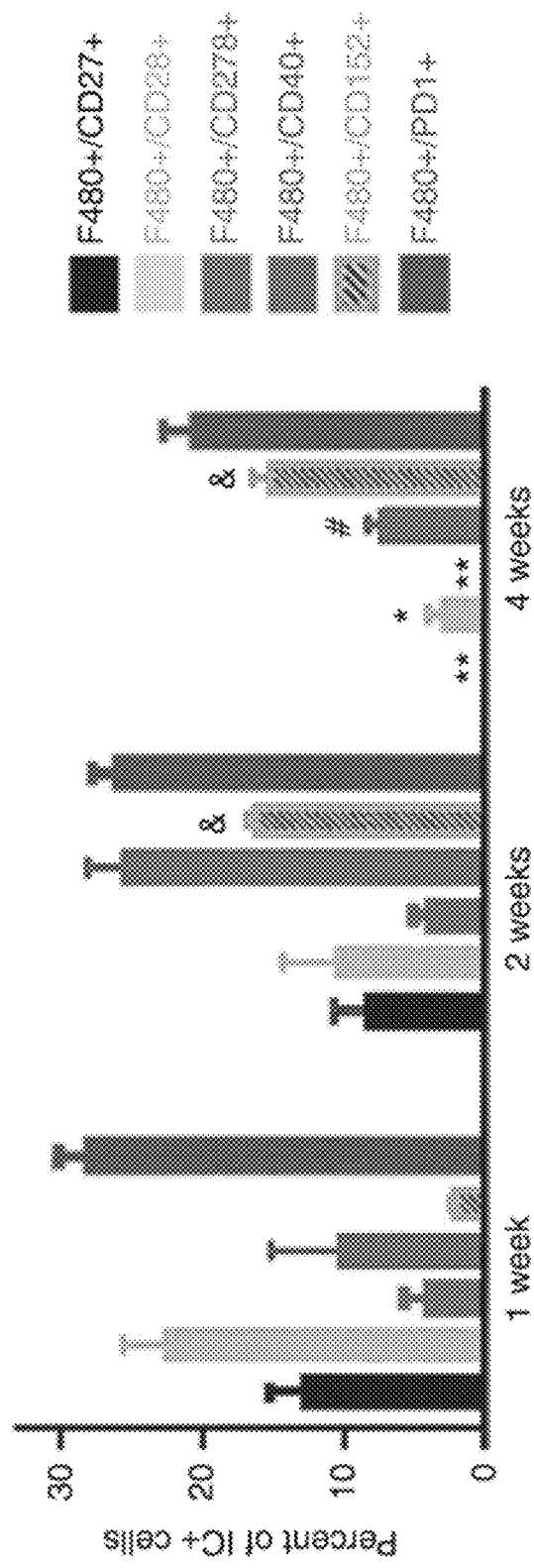
Figure 9:
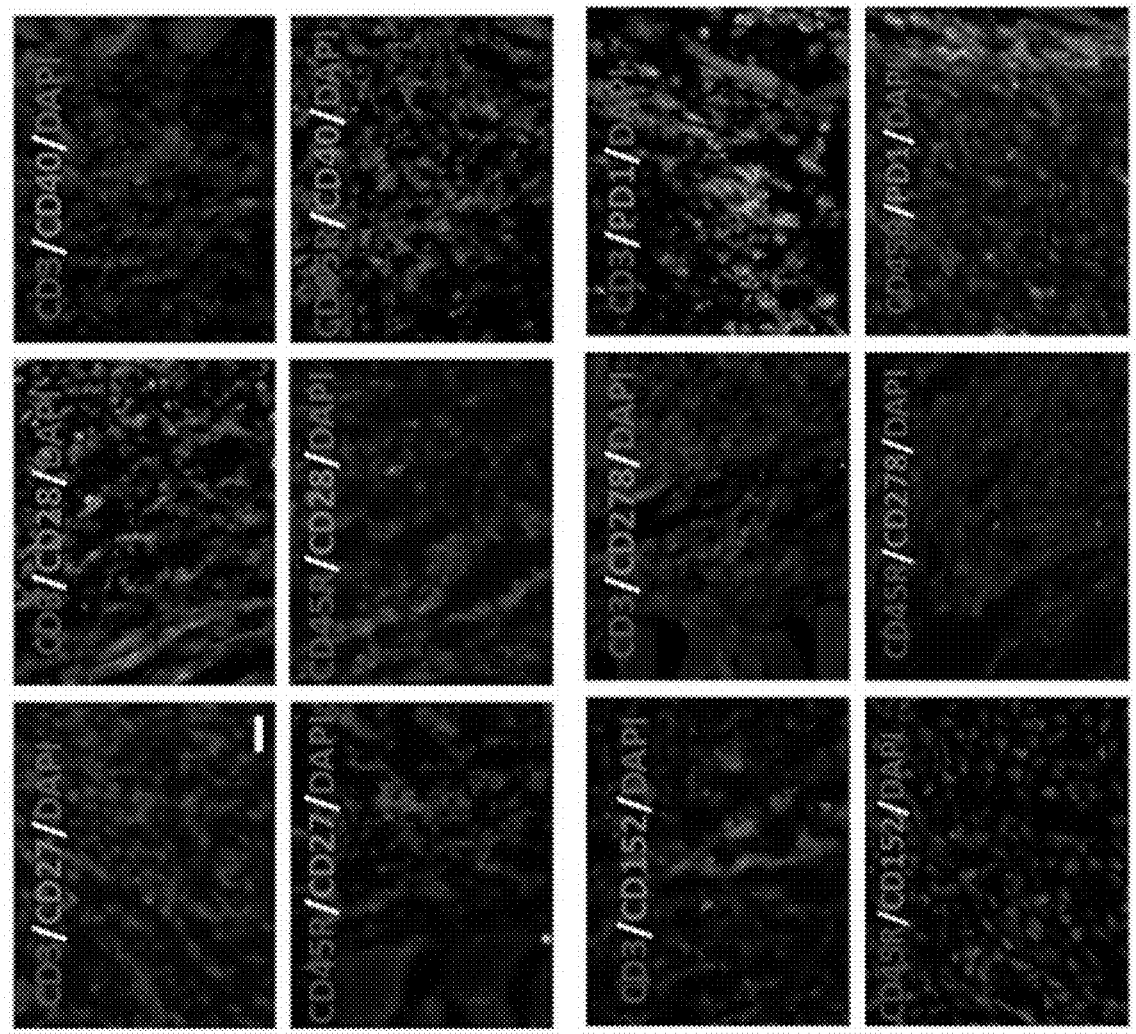
FIG. 9. Immune checkpoint proteins were rarely co-localized within lymphocytes. Contrary to our original expectation, immune checkpoint proteins were rarely co-localized within lymphocytes in lesional tissues of HO. Top panels: Immunofluorescence staining showing the co-localization of CD3 and ICs at 2W p.i. Bottom panels: Immunofluorescence staining showing the co-localization of CD45R and ICs at 2W p.i.

Dysregulation of ICs in HO. To directly test the central hypothesis that tissue damage, especially after traumatic injuries, induces IC dysregulation in susceptible mice, we next determined whether ICs are dysregulated in the HO process. We immunostained injury sites for ICs including stimulatory ICs (CD27, CD28, CD278, CD40), and inhibitory ICs (CD152, TIM3, PD1, and PDL1) at different times p.i. (FIG. 2a-c). Although the ICs had somewhat differing patterns of expression, in general the percentage of cells expressing stimulatory ICs was markedly increased in the early stages but decreased at later stages of HO. The time course of expression of inhibitory ICs was more variable with increases in some (TIM3 and PD1) inhibitory ICs occurring within the first week, whereas the percentage of cells expressing other inhibitory ICs was increased later during the HO process. Double staining with immune cell markers (F4/80) revealed that both stimulatory and inhibitory ICs were extensively co-expressed by F4/80+Mϕ (FIG. 3) but only rarely in lymphocytes (FIG. 9).

Figure 4:
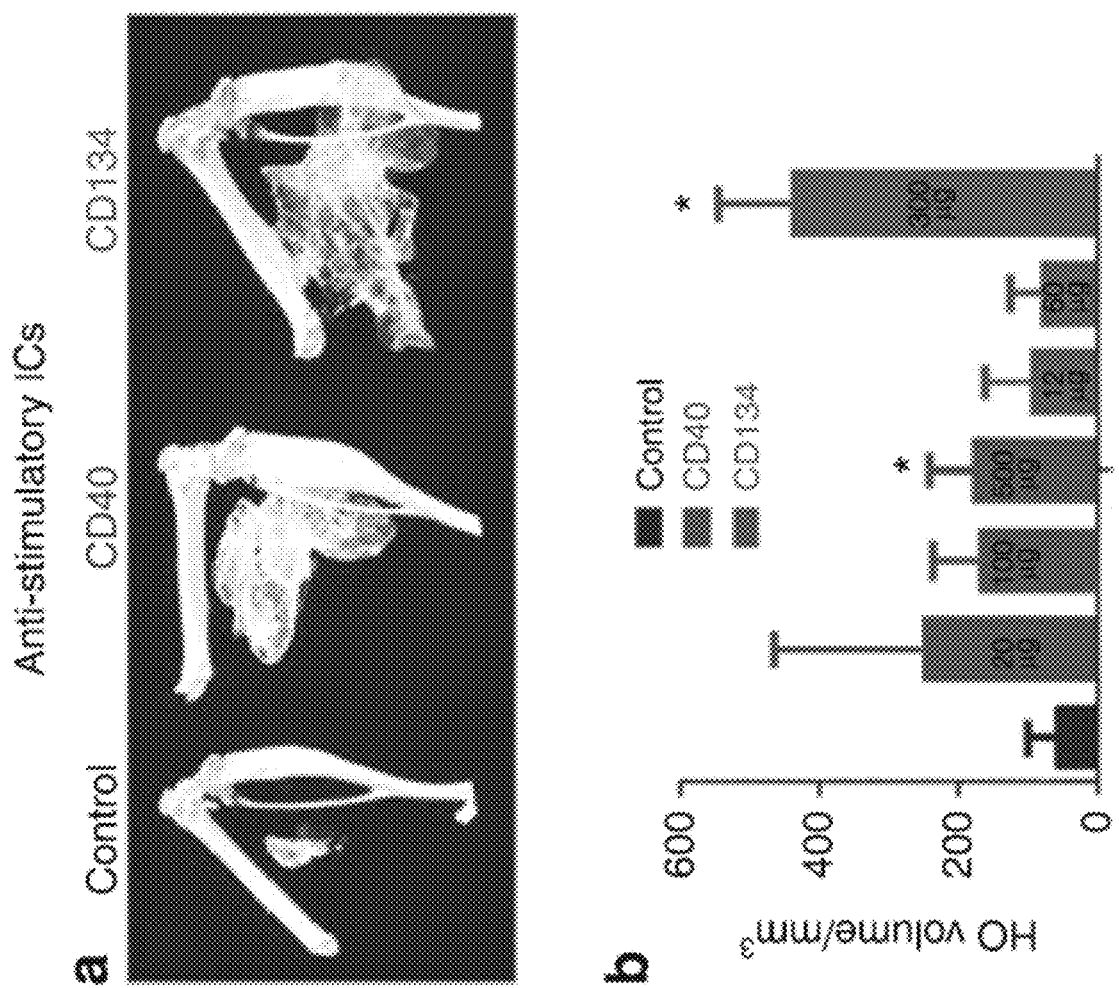
FIG. 4. Loss of function of inhibitory ICs blocks HO, while loss of function of stimulatory ICs facilitates HO. a, b Neutralizing antibodies against stimulatory ICs (CD40 and CD134) facilitated HO formation (n=3) *P<0.05 vs control group. c, d Neutralizing antibody against inhibitory ICs (PD1, PD-L1, and CD152) almost completely inhibited HO formation (n=3), *P<0.05 vs control group.
Figure 4:
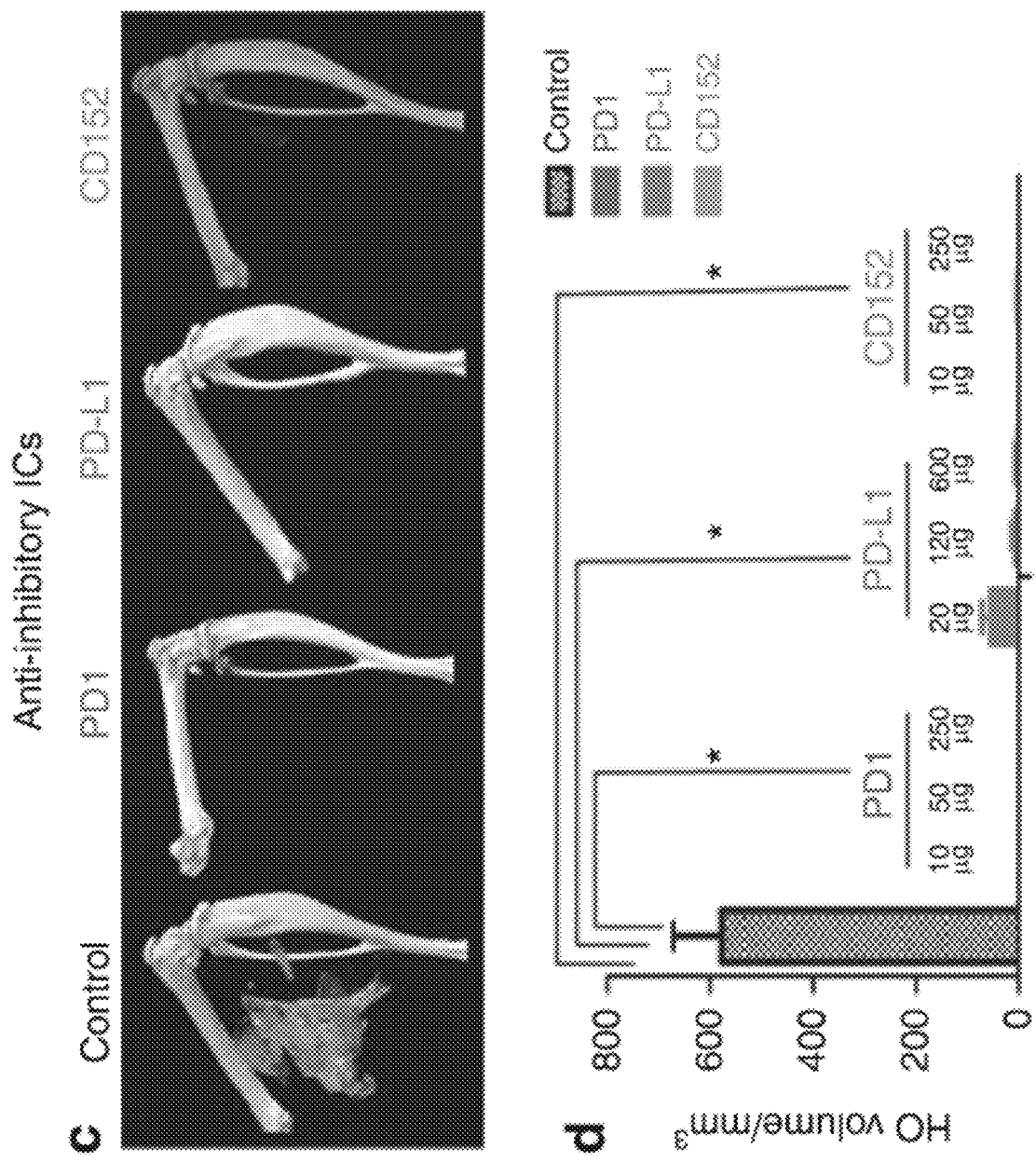
Figure 5:
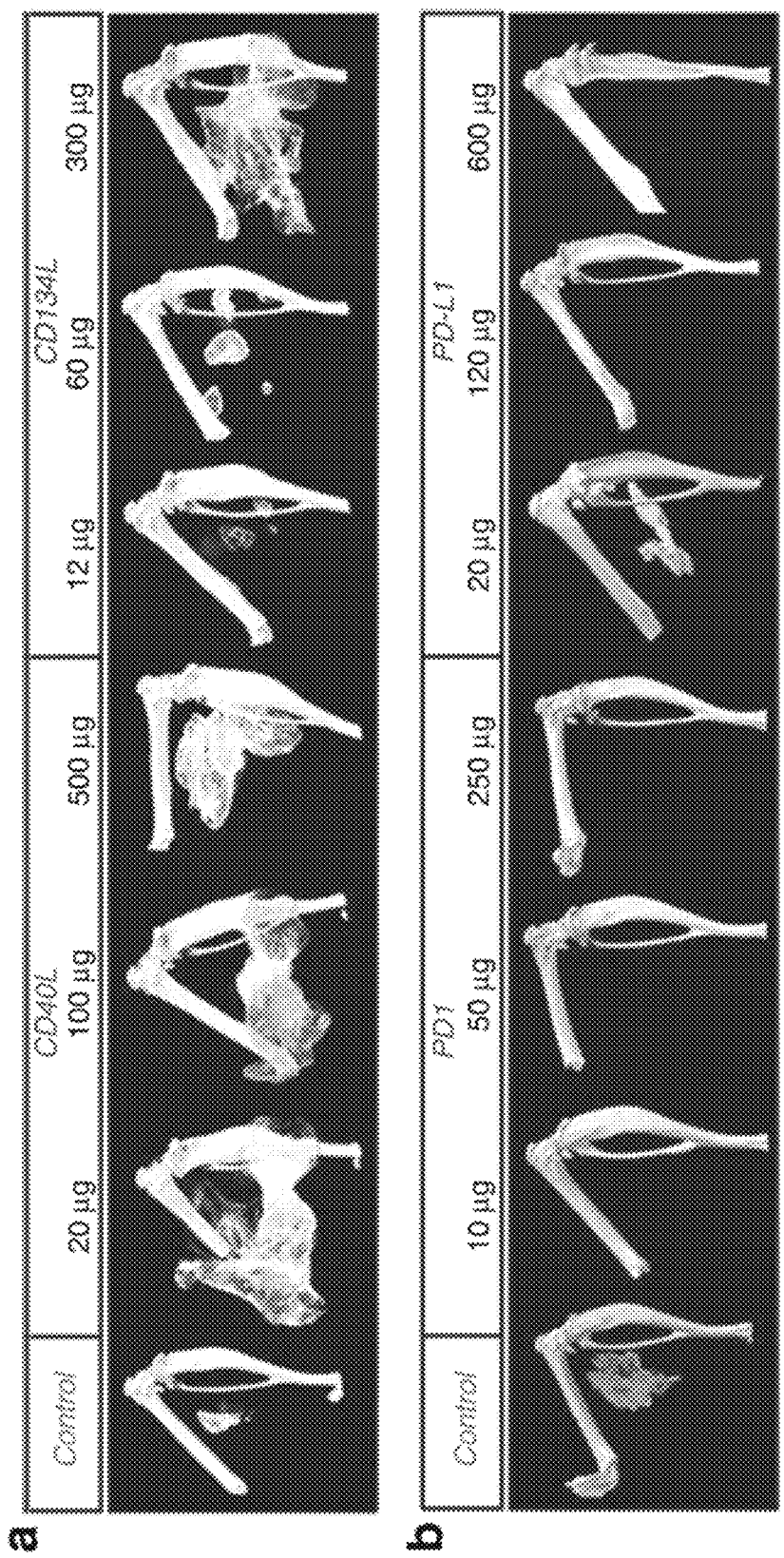
FIG. 5. Dose response of the effects of IC inhibition on HO and effects of PD1 antibody on CD206+/F480+ macrophage numbers and cytokine expression. a, b The effects of IC antibodies, particularly CD134L and PD-L1, on HO are dose dependent. c Effects of PD1 antibody (10 μg) on the number of CD206+/F480+ cells in tissue. Values are means±SEM. N=5. **Differs from other groups at P<0.01. d Cytokine mRNA expression in Nse-BMP mice with and without PD1 antibody. Values are expressed as fold-change from the WT level. N=4. *Differs from WT at P<0.05; **Differs from WT at P<0.01; &Differs from both other groups at P<0.02; $Differs from both other groups at P<0.05. Statistics were performed with ANOVA with Bonferroni's post hoc test.
Figure 5:
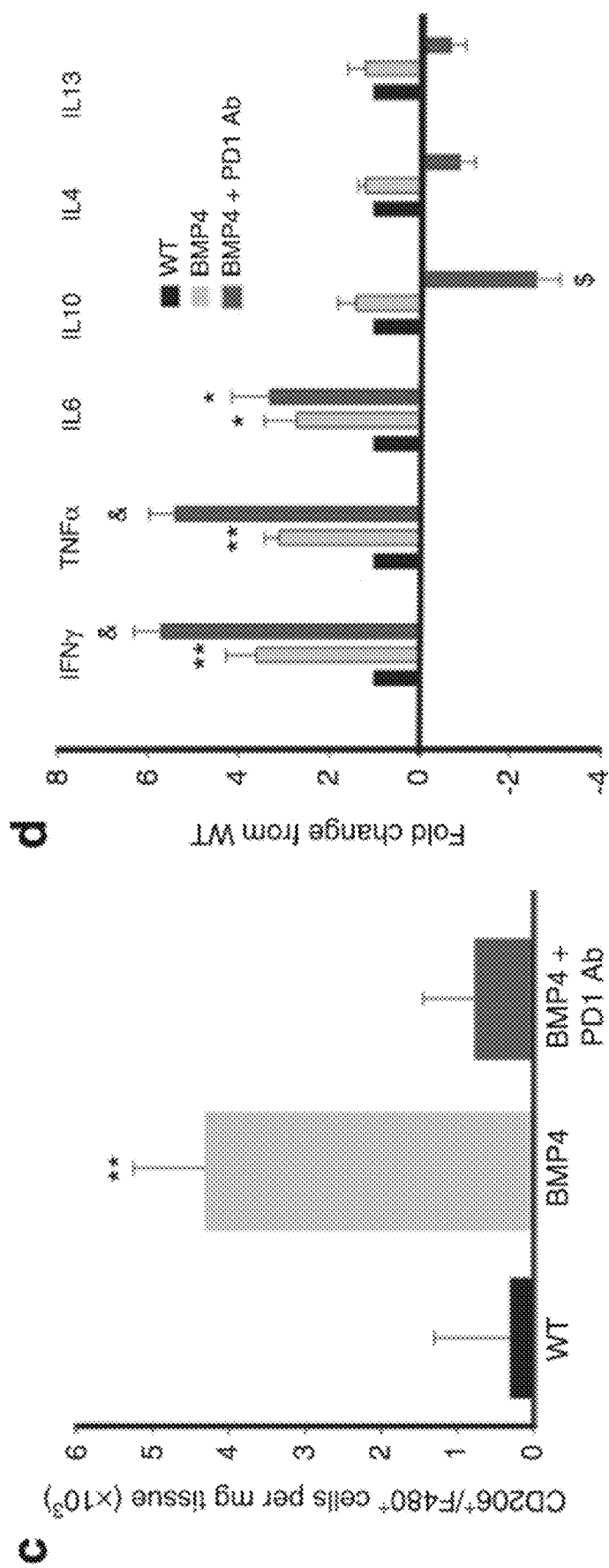

Neutralizing Abs against inhibitory ICs block HO. To functionally test the central hypothesis, we treated the mice with neutralizing Abs against stimulatory ICs (FIG. 4a, b) or inhibitory ICs (FIG. 4c, d) after injury. Typical three-dimensional (3D) reconstructed micro-computed tomographic (micro-CT) images shown in FIG. 4 demonstrate that neutralizing Abs against stimulatory ICs (CD40 and CD134) actually facilitated HO, while neutralizing Abs against inhibitory ICs (PD1, PD-L1, and CD152) inhibited HO, partly in a dose-dependent (FIG. 5) manner. Note that, in the studies shown in FIG. 4 of Abs against inhibitory ICs, most mice in the experimental groups did not develop HO at 1 month. To determine whether the treatments only delayed the HO process, the experiment was extended to 2 months. For this reason, the micro-CT images in FIG. 4c were taken at 2 months p.i., instead of 1 month p.i. (FIG. 4a). The HO volume difference between the control groups in (FIG. 4a) and (FIG. 4c) reflects this difference. The effects of neutralizing inhibitory ICs were profound with almost no mice developing HO even after 2 months (FIG. 4d). Neutralization of PD1 increased the expression of inflammatory cytokines (IFN-γ and TNF-α) in BMP4-induced Mϕ, decreased expression of anti-inflammatory cytokines (IL-10), and decreased the population of CD206+Mϕ, suggesting polarization toward a more inflammatory phenotype (FIG. 5).

Figure 6:
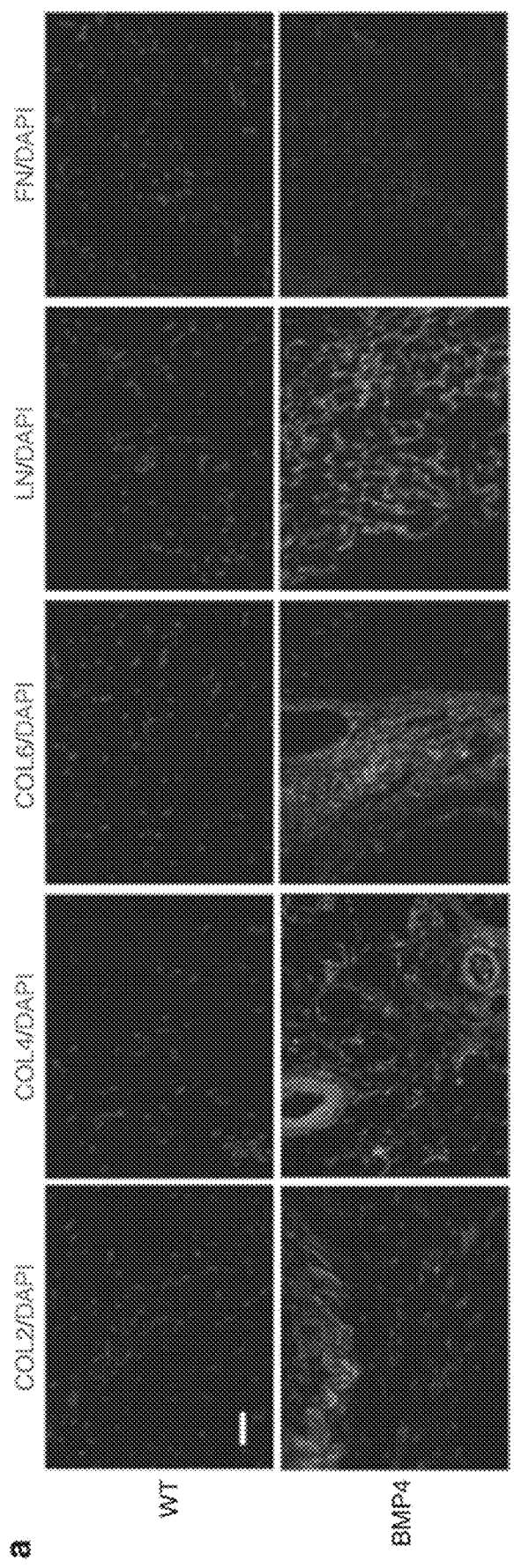
FIG. 6. Increased deposition of ECM proteins in HO lesions is associated with decreased expression of Adamts19 and MMP12 deficiency in macrophages. a, b Immunostaining revealed that deposition of ECM proteins (collagen 2, 4, 6, laminin, and fibronectin) is increased in HO lesions. (n=3 per group), *P<0.05 vs group of WT with injury. c Western blot analysis confirms the increase in ECM proteins in injury sites in Nse-BMP4 mice. d qPCR results showed that Adamts19 and MMP12 expression was significantly decreased in F4/80 macrophages from Nse-BMP4 mice with injury (n=3 per group), *P<0.05 vs group of WT without injury, #P<0.05 vs group of WT with injury at 1 week p.i.
Figure 6:
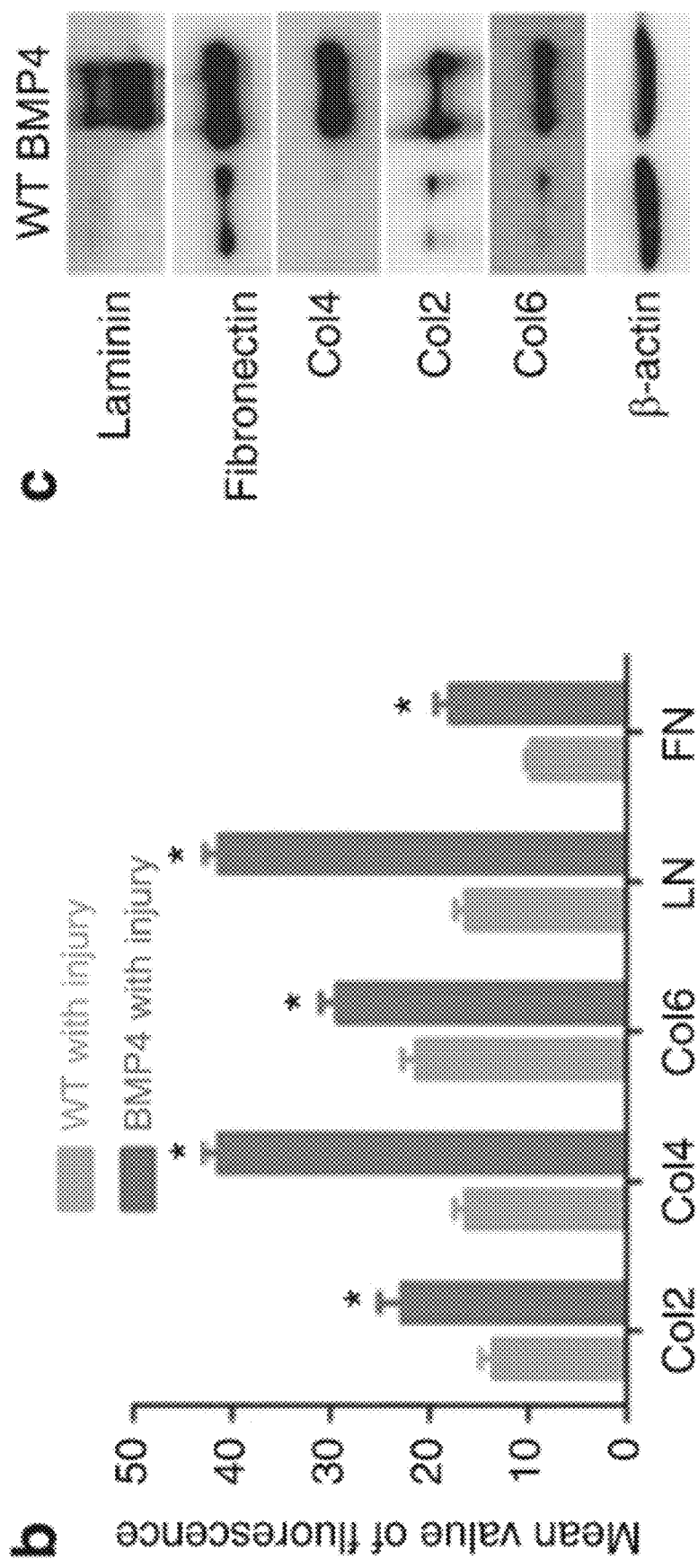
Figure 6:
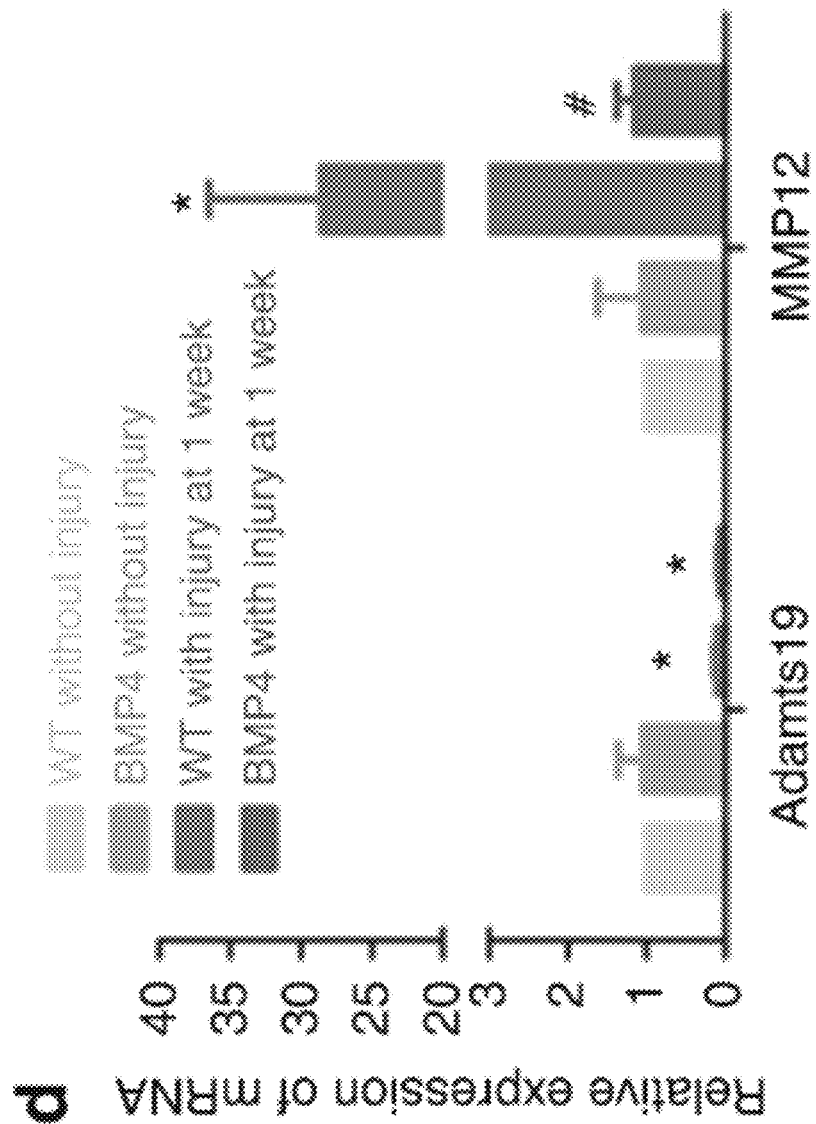

HO is associated with excessive collagen deposition and with changes in metallopeptidase expression by macrophages. We found that increased deposition of extracellular matrix (ECM) proteins is a consistent feature of the early phases of HO (FIG. 6a-c). In view of the central role of Mϕ in HO, we questioned whether they may alter the ECM during the HO process. Matrix metallopeptidase 12 (MMP12) and a metalloproteinase with thrombospondin motifs 19 (Adamts19) are important ECM components involved in the breakdown of ECM. Expression by F4/80 Mϕ of Adamts19 was reduced after injury in WT mice but MMP12 expression was significantly increased. However, the increase in MMP12 expression did not occur after injury to Nse-BMP4 mice (FIG. 6d), suggesting a possible mechanism for the increase in ECM proteins in the lesional tissues.

Discussion

Figure 7:
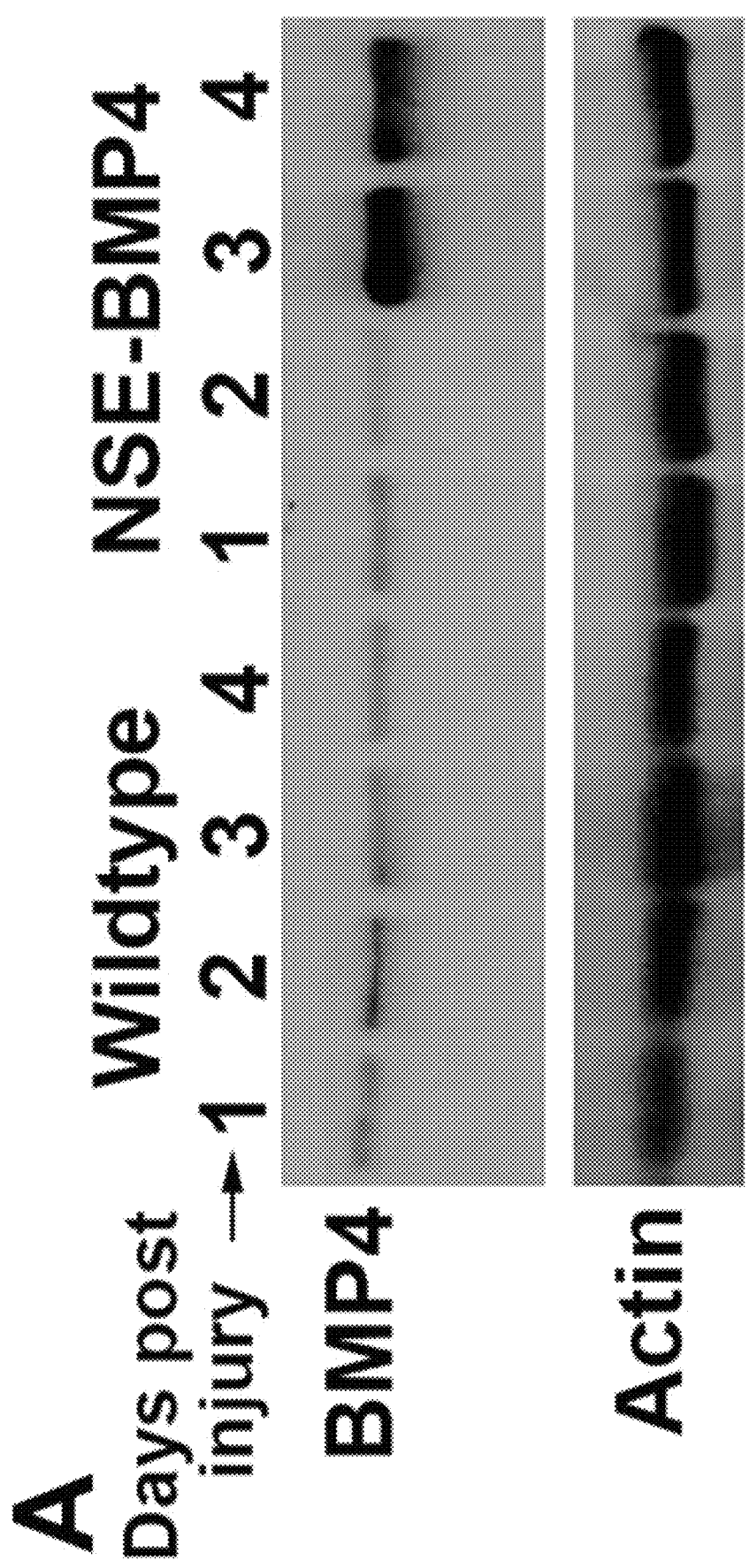
FIG. 7. Expression of BMP4 and histological features of lesional tissues of WT and Nse-BMP4 mice. A) Western analysis for BMP4 expression at the lesion site in WT and NSE-BMP4 mice. There are no differences in expression for the first two days after injury, but a large increase occurred on day 3 in NSE-BMP4 mice. B-C) H&E staining showing the early morphological features of injured muscles at day 3 & 7 p.i. in WT mice, D-G) H&E staining showed the typical morphological features of HO from the inflammatory stage to the fibroproliferative stage (1 week after injury), the condensation and chondrogenesis stage (2 weeks after injury) and finally endochondral bone formation injury (4 weeks after injury).
Figure 7:
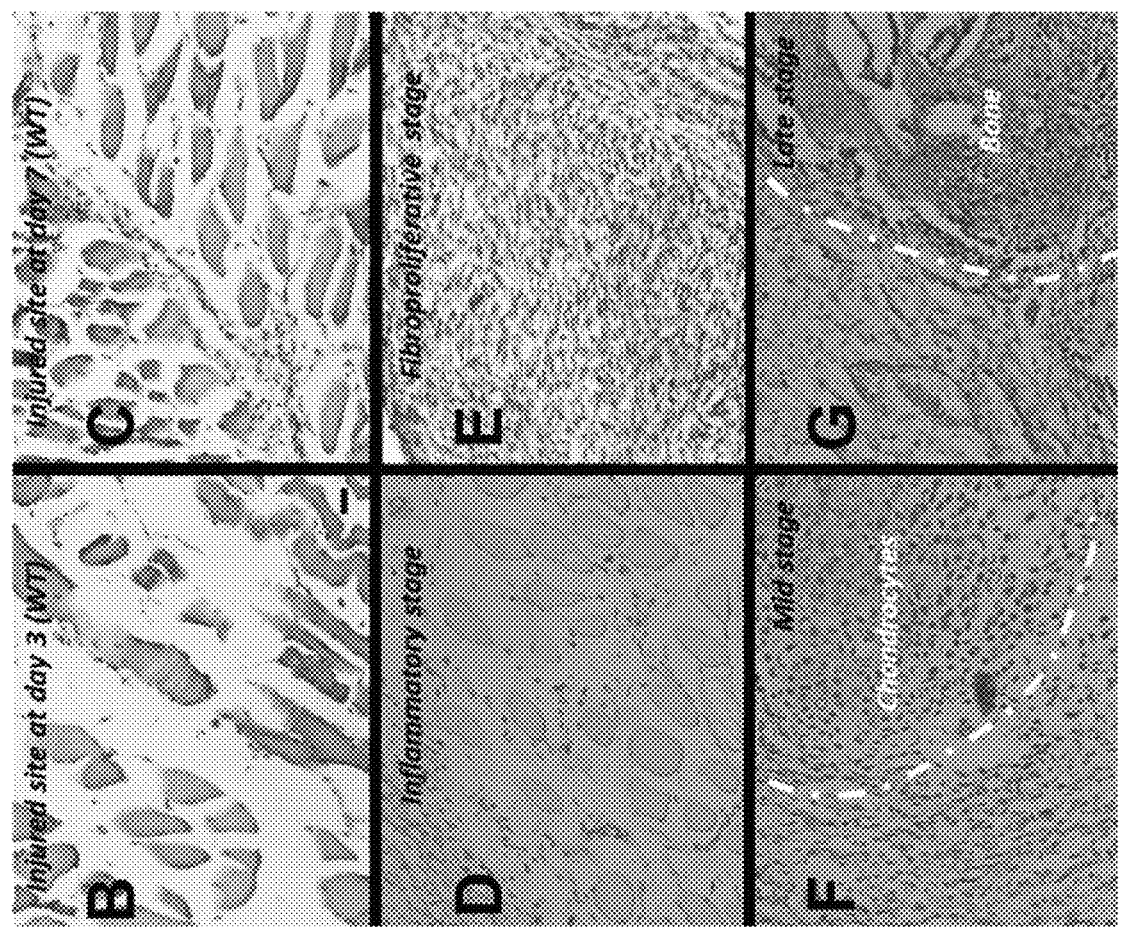

HO typically is preceded by trauma followed by an aggravated early acute injury response, and then persistent low-grade inflammation.[26] However, the cascade of events leading to HO is still largely unknown, especially the early triggering event. The predominant view in the field at present is that BMP receptor signaling, mediated by BMP2/4/6/7 and/or activin, initiates the effects of the traumatic insults that lead to HO. The hypothesis underlying our current studies, and our experimental findings, challenge this view. Although BMP receptor signaling clearly plays a central role in HO, we find that BMP signaling is a later rather than early part of the signaling cascade that culminates in HO. Among over a dozen BMP-overexpressing transgenic lines, the Nse-BMP4 line utilized in the current studies is the only one that recapitulates the hallmarks of both aHO and FOP.[11,22] This reflects the characteristics of the Nse promoter that drives the transgene construct. In Nse-BMP4 mice, the Nse transgene is induced in Mϕ by injury, but the injury-induced expression of BMP4 does not become significant until 3 days p.i. (FIG. 7). This suggests that increased BMP signaling is not the initiating event in Nse-BMP4 mice but rather a necessary factor for propagating the pathophysiologic process.

Previous studies have shown that, unlike normal skeletogenesis, both innate and adaptive immunities contribute to HO.[11] In particular, Mϕ are both abundant and persistent in local HO lesions, and limiting the influx of monocytes/Mϕ reduces or prevents experimental HO.[11] This suggests an essential early role for Mϕ in triggering HO. We found that both stimulatory and inhibitory ICs were expressed by Mϕ in HO lesions. In general, the percentage of cells expressing stimulatory ICs was markedly increased in the early stages but decreased at later stages of HO, whereas the percentage of cells expressing inhibitory ICs was more variable with some increased earlier and some later during the HO process. Interfering with the expression of inhibitory ICs resulted in a truly remarkable reduction in HO with almost total prevention of HO even 2 months post-injury in the Nse-BMP4 mice. Conversely, interfering with the expression of stimulatory ICs markedly increased the severity of the HO. These observations highlight the central role of ICs in the altered immune homeostasis that leads to HO.

The observation that immune suppressants such as Rapamycin and Ebselen suppress HO would seem to suggest that overactive immune responses are responsible for HO. However, the findings that loss of function of stimulatory ICs facilitated HO, whereas loss of function of inhibitory ICs inhibited HO would seem to suggest that depressed immune responses are responsible. What underlies these seemingly contradictory sets of observations? We found that the percentage of CD206+/F4/80+Mϕ in lesion sites increased progressively with time. In fact, <1% of the Mϕ expressed CD206 at the time of injury while about 90% of the cells expressed CD206 within several weeks. Similarly, there was a conversion in the ICs expressed by the Mϕ from stimulatory to inhibitory ones. This suggests a dynamic biphasic process, i.e., overactive early and depressed later immune responses that both are necessary preconditions for the subsequent HO. Thus blocking either phase may be sufficient to prevent HO.

In earlier studies, we identified dysregulation of local stem/progenitor cells as a common cellular mechanism for HO,[11] and many subsequent studies have characterized both the lineage of the stem cells and the cellular and molecular components of the stem cell niche that presdisposes them to osteogenic differentiation.[23,25,27-32] Stem/progenitor cell differentiation is greatly influenced by the ECM in which the cells reside, and increased deposition of ECM proteins is a consistent feature of the early phases of HO.[33-37] In view of the central role of Mφ in HO,[38-41] we questioned whether they may alter the ECM during the HO process. We found that expression by F4/80 Mφ of both MMP12 and Adamts19 was reduced after injury in Nse-BMP4 mice, whereas MMP12 increased in WT mice, suggesting a possible mechanism for the increase in ECM proteins in the lesion.

Although it is always difficult to extrapolate from animal models of disease to humans, the cellular and molecular features of human HO are very similar to what is observed in Nse-BMP4 mice.[28] Thus we hypothesize that a BMP-dependent, injury-induced stem cell niche is a common mechanism of HO[28] and that the altered immune homeostasis observed in the animal model are part of the process in humans. Importantly, we specifically used FDA-approved IC inhibitors in these studies to enhance the potential translational implications. Our findings suggest that treatment with IC Abs, in particular those that target inhibitory ICs, may provide a therapeutic approach to this currently untreatable clinical problem.

Materials and Methods

Animals and injury models. Nse-BMP4 transgenic mice, described previously,[11,12,22-24] express BMP4 under the control of promoter of Nse. HO was induced by intramuscular injection of cardiotoxin (Sigma), according to previous reports.[11,12,23,24] All animal experiments in this study were approved by the Animal Care and Use Committees at Anhui Medical University (Protocol: LLSC20140042) and Northwestern University (Protocol: IS00001002).

Quantification of local immune cell infiltration after injury. Immunostaining for different markers were performed as previously described.[11,25] Briefly, sections were pre-fixed with 4% paraformaldehyde in phosphate-buffered saline (PBS). Nonspecific binding was blocked with 10% normal serum diluted in 1% bovine serum albumin (BSA; Jackson ImmunoResearch Laboratories, West Grove, PA) and 0.25% Triton X-100 (Sigma) for 1 h at room temperature. The sections then were incubated with primary Abs diluted with 1% BSA+0.25% Triton X-100 at 4° C. overnight. After washing, the sections were incubated with appropriate secondary Abs (Alexa Fluor 488, Alexa Fluor 594 conjugated Abs, Thermo Fisher Scientific) diluted with 1% BSA+0.25% Triton X-100 in a dark at room temperature for 2 h and counterstained with 4, 6-diamidino-2-phenylindole (1:5 000). All fluorescent images were taken using ZEISS Axio Observer (Carl Zeiss, Germany). Signals from all channels were collected separately and overlaid in DPViewer.

Functional modulation of immune responses with immunosuppressants or IC blockade (neutralizing Abs against ICs). Nes-BMP4 mice (n=4) were treated with Rapamycin (5 mg kg$^{-1}$) or Ebselen (1 mg kg$^{-1}$), every other day for 2 weeks (8 injections) through intraperitoneal (i.p.) injection starting 1 day p.i. Control Nse-BMP4 mice were treated with vehicle on the same schedule. Every other day, dosing was used to minimize trauma to skin and abdominal muscle so that HO was not triggered by the injections. For IC blockade, the mice were treated with specific neutralizing Abs against stimulatory ICs, including CD40L (BioxCell, at the dosages of 20, 100, and 500 μg per injection) and CD134L (BioxCell, at the dosages of 60, 120, and 300 μg per injection), and inhibitory ICs, including CTLA-4 (BioxCell, at the dosages of 10, 50, and 250 μg per injection), PD1 (BioxCell, at the dosages of 10, 50, and 250 μg per injection), and PD-L1 (BioxCell, at the dosages of 24, 120, and 600 μg per injection), through the tail vein every other day for 1 week (4 injections) starting 1 day p.i.

X-ray and micro-CT imaging. For X-ray, mice were anesthetized by 1% pentobarbital (150 μL i.p.) and the images of radio-opaque HO were acquired by whole-body X-ray examination at 38 kv, 28 mA, 30 s (Bruker, USA). To quantitatively measure HO volume, micro-CT (PerkinElmer, USA) was used with the setting parameters of 180° rotation, constant 90 kv voltage, and voxel size 72 μm, and the 3D images were reconstructed by the software package of the system.

Western blotting (WB). Lesional tissues or isolated Mφ were lysed with RIPA buffer (Beyotime Biotechnology, China). Protein concentration was assessed by Bradford assay (Bio-Rad laboratories, USA). Protein samples (20 μg) were resolved using 8% polyacrylamide gel and electrophoretically transferred to nitrocellulose and then blocked with non-fat milk in 0.1% Tween-20 in PBS for 1 h. Membranes were then incubated with primary Abs at room temperature for 1.5 h, and after washing, the membranes were incubated with horseradish peroxidase-conjugated secondary Abs. The specific signals were detected using the enhanced chemiluminescence western blot detection system (Odyssey, USA) after washing, following the manufacturer's instructions. β-Actin was used as the loading control.

RNA extraction and qRT-PCR analysis. An MirVana miRNA Kit (Takara, China) was used to extract total RNA from lesional tissues and Mφ following the manufacturer's instructions. PrimeScriptRT Reagent Kit (Takara, China) was used to synthesize the first-strand cDNA. Expression of various genes was quantified by the Real-time PCR Mixture assays (Takara, China). β-Actin was used as the internal control.

Study of lesional macrophages. For tissue Mφ, F4/80+Mφ were sorted from injured tissues at different times through a MACS Kit (Miltenyi, USA), according to the manufacturer's instruction, and the F4/80+Mφ were further analyzed by flow cytometry (BD, USA), using CD206 Ab (BD Pharmingen, USA) diluted with flow cytometry buffer (PBS+0.5% BSA+0.09% Sodium Azide). Flow cytometric data were analyzed by the FlowJo software (Tree Star, Inc).

Statistical analyses. Data are reported as means±standard deviation. Statistical analyses between two groups were performed using Student's t test via SPSS 16.0 (SPSS Science, Chicago, IL). Statistical analyses between multiple groups were performed using one-way analysis of variance (ANOVA) or ANOVA with repeated measures followed by Bonferroni's post hoc test. P<0.05 was considered as statistically significant.

References

1. Sakellariou V I, Grigoriou E, Mavrogenis A F, Soucacos P N, Papagelopoulos P J. Heterotopic ossification following traumatic brain injury and spinal cord injury: insight into the etiology and pathophysiology. J Musculoskelet Neuronal Interact. 2012; 12(4):230-40.

2. Xu R, Hu J, Zhou X, Yang Y. Heterotopic ossification: Mechanistic insights and clinical challenges. Bone. 2017.

3. Pacifici M. Acquired and congenital forms of heterotopic ossification: new pathogenic insights and therapeutic opportunities. Curr Opin Pharmacol. 2018; 40:51-8.

4. Dey D, Wheatley B M, Cholok D, Agarwal S, Yu P B, Levi B, et al. The traumatic bone: trauma-induced heterotopic ossification. Transl Res. 2017; 186:95-111.

5. Legosz P, Drela K, Pulik L, Sarzynska S, Maldyk P. Challenges of heterotopic ossification-Molecular background and current treatment strategies. Clin Exp Pharmacol Physiol. 2018; 45(12):1229-35.

6. Hurlimann M, Schiapparelli F F, Rotigliano N, Testa E, Amsler F, Hirschmann M T. Influence of surgical approach on heterotopic ossification after total hip arthroplasty—is minimal invasive better? A case control study. BMC Musculoskelet Disord. 2017; 18(1):27.

7. Zeckey C, Hildebrand F, Frink M, Krettek C. Heterotopic ossifications following implant surgery—epidemiology, therapeutical approaches and current concepts. Semin Immunopathol. 2011; 33(3):273-86.

8. Huning I, Gillessen-Kaesbach G. Fibrodysplasia ossificans progressiva: clinical course, genetic mutations and genotype-phenotype correlation. Mol Syndromol. 2014; 5(5):201-11.

9. Jiang J X. Posttraumatic stress and immune dissonance. Chin J Traumatol. 2008; 11(4):203-8.

10. Czura C J, Friedman S G, Tracey K J. Neural inhibition of inflammation: the cholinergic anti-inflammatory pathway. J Endotoxin Res. 2003; 9(6):409-13.

11. Kan L, Liu Y, McGuire T L, Berger D M, Awatramani R B, Dymecki S M, et al. Dysregulation of local stem/progenitor cells as a common cellular mechanism for heterotopic ossification. Stem Cells. 2009; 27(1):150-6.

12. Kan L, Mutso A A, McGuire T L, Apkarian A V, Kessler J A. Opioid signaling in mast cells regulates injury responses associated with heterotopic ossification. Inflamm Res. 2014; 63(3):207-15.

13. Ranganathan K, Agarwal S, Cholok D, Loder S, Li J, Sung Hsieh H H, et al. The role of the adaptive immune system in burn-induced heterotopic ossification and mesenchymal cell osteogenic differentiation. J Surg Res. 2016; 206(1):53-61.

14. Jung K, Choi I. Emerging Co-signaling Networks in T Cell Immune Regulation. Immune Netw. 2013; 13(5):184-93.

15. Sperk M, Domselaar R V, Neogi U. Immune Checkpoints as the Immune System Regulators and Potential Biomarkers in HIV-1 Infection. Int J Mol Sci. 2018; 19(7).

16. Riva A, Chokshi S. Immune checkpoint receptors: homeostatic regulators of immunity. Hepatol Int. 2018.

17. Cicerone C, Nenna R, Pontone S. Th17, intestinal microbiota and the abnormal immune response in the pathogenesis of celiac disease. Gastroenterol Hepatol Bed Bench. 2015; 8(2):117-22.

18. Kohn J. Abnormal immune response in burns. Postgrad Med J. 1972; 48(560):335-7.

19. Jasiulionis M G. Abnormal Epigenetic Regulation of Immune System during Aging. Front Immunol. 2018; 9:197.

20. Qureshi A T, Dey D, Sanders E M, Seavey J G, Tomasino A M, Moss K, et al. Inhibition of Mammalian Target of Rapamycin Signaling with Rapamycin Prevents Trauma-Induced Heterotopic Ossification. Am J Pathol. 2017; 187(11):2536-45.

21. Wendel A, Kuesters S, Tiegs G. Ebselen—an in vivo immune response modifier. Biomed Environ Sci. 1997; 10(2-3):253-9.

22. Kan L, Hu M, Gomes W A, Kessler J A. Transgenic mice overexpressing BMP4 develop a fibrodysplasia ossificans progressiva (FOP)-like phenotype. Am J Pathol. 2004; 165(4):1107-15.

23. Kan L, Lounev V Y, Pignolo R J, Duan L, Liu Y, Stock S R, et al. Substance P signaling mediates BMP-dependent heterotopic ossification. J Cell Biochem. 2011; 112(10): 2759-72.

24. Kan L, Peng C Y, McGuire T L, Kessler J A. Glast-expressing progenitor cells contribute to heterotopic ossification. Bone. 2013; 53(1):194-203.

25. Kan C, Chen L, Hu Y, Ding N, Li Y, McGuire T L, et al. Gli1-labeled adult mesenchymal stem/progenitor cells and hedgehog signaling contribute to endochondral heterotopic ossification. Bone. 2017.

26. Kraft C T, Agarwal S, Ranganathan K, Wong V W, Loder S, Li J, et al. Trauma-induced heterotopic bone formation and the role of the immune system: A review. J Trauma Acute Care Surg. 2016; 80(1):156-65.

27. Kan C, Chen L, Hu Y, Ding N, Lu H, Li Y, et al. Conserved signaling pathways underlying heterotopic ossification. Bone. 2017.

28. Kan C, Ding N, Yang J, Tan Z, McGuire T L, Lu H, et al. BMP-dependent, injury-induced stem cell niche as a mechanism of heterotopic ossification. Stem Cell Res Ther. 2019; 10(1):14.

29. Kan L, Kessler J A. Evaluation of the cellular origins of heterotopic ossification. Orthopedics. 2014; 37(5):329-40.

30. Wang H, Shore E M, Pignolo R J, Kaplan F S. Activin A amplifies dysregulated BMP signaling and induces chondro-osseous differentiation of primary connective tissue progenitor cells in patients with fibrodysplasia ossificans progressiva (FOP). Bone. 2017.

31. Agarwal S, Loder S J, Cholok D, Peterson J, Li J, Breuler C, et al. Scleraxis-Lineage Cells Contribute to Ectopic Bone Formation in Muscle and Tendon. Stem Cells. 2017; 35(3):705-10.

32. Kaplan, F. S., Pignolo, R. J. & Shore, E. M. Granting immunity to FOP and catching heterotopic ossification in the Act. Semin. Cell Dev. Biol. 49, 30-36 (2016).

33. Haupt J, Stanley A, McLeod C M, Cosgrove B D, Culbert A L, Wang L, Mourkioti F, Mauck R L, Shore E M. ACVR1R206H FOP mutation alters mechanosensing and tissue stiffness during heterotopic ossification. Mol Biol Cell. 2019; 30(1):17-29

34. Rodenberg E, Azhdarinia A, Lazard Z W, Hall M, Kwon S K, Wilganowski N, et al. Matrix metalloproteinase-9 is a diagnostic marker of heterotopic ossification in a murine model. Tissue Eng Part A (2011) 17:2487-96. 10.1089/ten.tea.2011.00.

35. Crowgey E L, Wyffels J T, Osborn P M, Wood T T, Edsberg L E. A Systems Biology Approach for Studying Heterotopic Ossification: Proteomic Analysis of Clinical Serum and Tissue Samples. Genomics Proteomics Bioinformatics. 2018 June; 16(3):212-220.

36. Davis E L, Sonnet C, Lazard Z W, Henslee G, Gugala Z, Salisbury E A, Strecker E V, Davis T A, Forsberg J A, Davis A R, Olmsted-Davis E A. Location-dependent heterotopic ossification in the rat model: The role of activated matrix metalloproteinase 9. J Orthop Res. 2016 November; 34(11):1894-1904.

37. Meyers C, Lisiecki J, Miller S, Levin A, Fayad L, Ding C, Sono T, McCarthy E, Levi B, James A W. Heterotopic Ossification: A Comprehensive Review. JBMR Plus. 2019; 3(4):e10172.

38. Levesque J P, Sims N A, Pettit A R, Alexander K A, Tseng H W, Torossian F, Genêt F, Lataillade J J, Le Bousse-Kerdilès M C. Macrophages Driving Heterotopic Ossification: Convergence of Genetically-Driven and Trauma-Driven Mechanisms. J Bone Miner Res. 2018; 33(2):365-366.

39. Convente M R, Chakkalakal S A, Yang E, Caron R J, Zhang D, Kambayashi T, Kaplan F S, Shore E M Depletion of Mast Cells and Macrophages Impairs Heterotopic Ossification in an Acvr1R206H Mouse Model of Fibrodysplasia Ossificans Progressiva. J Bone Miner Res. 201833(2):269-282.

40. Kraft C T, Agarwal S, Ranganathan K, Wong V W, Loder S, Li J, Delano M J, Levi B. Trauma-induced heterotopic bone formation and the role of the immune system: A review. J Trauma Acute Care Surg. 2016 January; 80(1): 156-65.

41. Loder S J, Agarwal S, Chung M T, Cholok D, Hwang C, Visser N, Vasquez K, Sorkin M, Habbouche J, Sung H H, Peterson J, Fireman D, Ranganathan K, Breuler C, Priest C, Li J, Bai X, Li S, Cederna P S, Levi B. Characterizing the Circulating Cell Populations in Traumatic Heterotopic Ossification Am J Pathol. 2018; 188(11):2464-2473.

Example 2—Use of an Fetuin-A for the Therapeutic Invention of Heterotopic Ossification Abstract Heterotopic ossification (HO) is characterized by pathological bone formation outside of the normal skeleton, generally following tissue damage, such as traumatic brain injury, spinal cord injury, total hip arthroplasty, wartime trauma or other traumatic injuries. Following the acute injury, these patients typically develop persistent low-grade inflammation, chronic pain, unhealed wounds, restricted joint movement, nerve entrapment and diminished quality of life. Hereditary HO, such as fibrodysplasia ossificans progressiva (FOP), though rare, is much more devastating and life threatening. HO is a tremendous unmet medical need, because currently there is no decisive treatment. Therapies targeting this disorder have not been successful mainly because of lack of efficient way to control the immune response and the subsequent calcification. For the first time, we characterize the use of Fetuin-A in injury induced HO that specifically corrects the abnormal early injury response and the subsequent HO in an animal model of HO. We believe this invention will have direct clinical implications.

Applications

Applications of the disclosed technology may include, but are not limited to: (i) inhibition of heterotopic ossification (HO) in indicated outpatients; and (ii) prevention of potential HO formation that is induced by traumatic injury or surgery intra-operatively or post-operatively, as a prophylaxis, for example, in a medical institution environment.

Advantages

Advantages of the disclosed technology may include, but are not limited to: (i) the disclosed methods and compositions utilize Fetuin-A which is a mechanism-based treatment for injury-induced heterotopic ossification (HO); (ii) the disclosed methods of administering Fetuin-A are extremely convenient to perform in the scenarios of traumatic injuries and/or surgeries, as a prophylaxis; and (iii) side-effects of exogenous Fetuin-A have not been observed or reported, and as such, the safety profile of the disclosed methods is extremely favorable.

Description

The inventors have used exogenous Fetuin-A to treat and inhibit heterotopic ossification (HO) that has been induced by traumatic injury and to correct an abnormal injury response.

Introduction

Heterotopic ossification (HO), acquired or hereditary, is characterized by pathological bone formation outside of the normal skeleton, generally following tissue damage. For example, acquired HO (aHO), is commonly triggered by traumatic brain injury, spinal cord injury, total hip arthroplasty, wartime trauma or other traumatic injuries. The incidence of aHO is relatively high (about 11% in TBI, 20% in SCI, 14-35% after major elbow trauma, and 4.7% after hip arthroscopy). Following the acute injury, these patients typically develop persistent low-grade inflammation, chronic pain, unhealed wounds, restricted joint movement, nerve entrapment and diminished quality of life. Hereditary HO, such as fibrodysplasia ossificans progressiva (FOP), though rare, is much more devastating and life threatening. Notably, even though FOP is caused by gain-of-function mutation of the type 1 bone morphogenetic protein (BMP) receptor, ACVR1 (also known as ALK2), the initiation of the HO process in FOP is similarly triggered by abnormal immune responses to minor injuries (also called flare-up) followed by persistent low grade inflammation. In previous studies we found that both innate immune responses and adaptive immunity play key roles in the pathological process of HO. Similarly, recent studies also have shown that disrupted adaptive immune responses are closely associated with HO formation in mice following burn injury and Achilles tenotomy.

Multifunctional glycoprotein fetuin-A (FA), also known as a2-HS glycoprotein (AHSG), plays prominent roles in numerous physiological and pathophysiological conditions. The fact that FA-deficient mice develop widespread soft-tissue calcification and have malformed skeleton bones proved the decisive role of FA both in ectopic calcification and skeletal bone formation. In addition, FA is also known to 1) be essential for bone formation and remodeling; 2) be a positive or negative acute phase protein (APP) that plays a pro-inflammatory or anti-inflammatory role, context-dependently; 3) be an important metabolic regulator that might modulate different disease process.

This study will focus mainly on the role of FA in HO, and the practical goal of this study is to find translatable novel interventions that could be viable prophylaxis and therapy for HO. The central hypothesis is that FA is dysregulated in the context of traumatic injuries, which might contribute to HO through multiple mechanisms, i.e., indirectly, FA dysregulation might precondition the disease process via dysregulating the immunometabolic pathways, which in turn, might directly up-regulate the ossification/osteogenesis process and increase the bone turnover.

To test this hypothesis and explore potential translational applications, this study 1) first determined that FA is closely associated with HO in the lesional tissues through immunohistochemistry (IHC) approach; 2) clarified FA is a highly specific osteogenic biomarker through detailed co-localization study; 3) confirmed that FA level was downregulated in the context of injury induced HO, and 4), functionally tested that injection of exogenous pure FA could inhibit injury induced HO. Overall, our study strongly suggested that FA may potentially provide a practical therapeutic approach to injury induced HO.

Results

Figure 10:
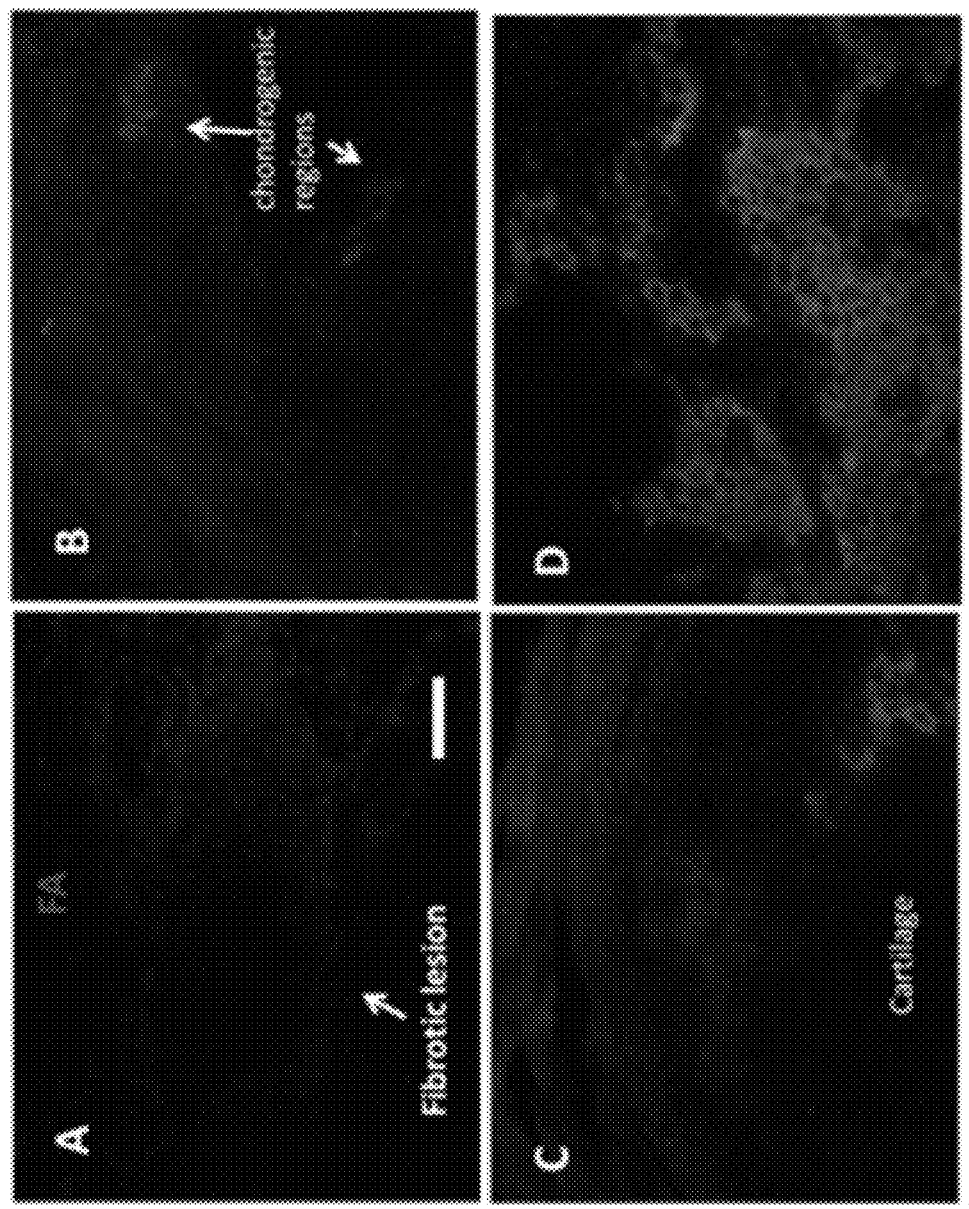
FIG. 10. FA is a specific biomarker of ossification associated with HO. (A-E) representative sequential images of FA stained lesional tissues from early to late stages of HO found that FA is consistently enriched in lesional tissues from late chondrogenic stages onward. F) Comparing the FA staining signals of HO and that of the skeletal bone (outlined by broken white lines) within the same low power image (pixel density in HO area was >3 times higher than that of skeletal long bone). G) Representative high power images of FA staining of skeletal bone (femur) found that FA was enriched in bone matrix, not in bone marrow. H) when we compared the adjusted concentration of FA in the lesional tissues (μg/mg total protein) with that of the skeletal bone through ELISA, we found a trend that HO has higher level of FA than that of skeletal bone. I) Adjusted FA concentrations in skeletal bone of Nse-BMP4 with HO and WT were similar. J) Liver section was used as a positive control of FA staining. Panels (A-E,G&H) are on the same scale, and (F) is a low power image. Bar=100 μm.
Figure 10:
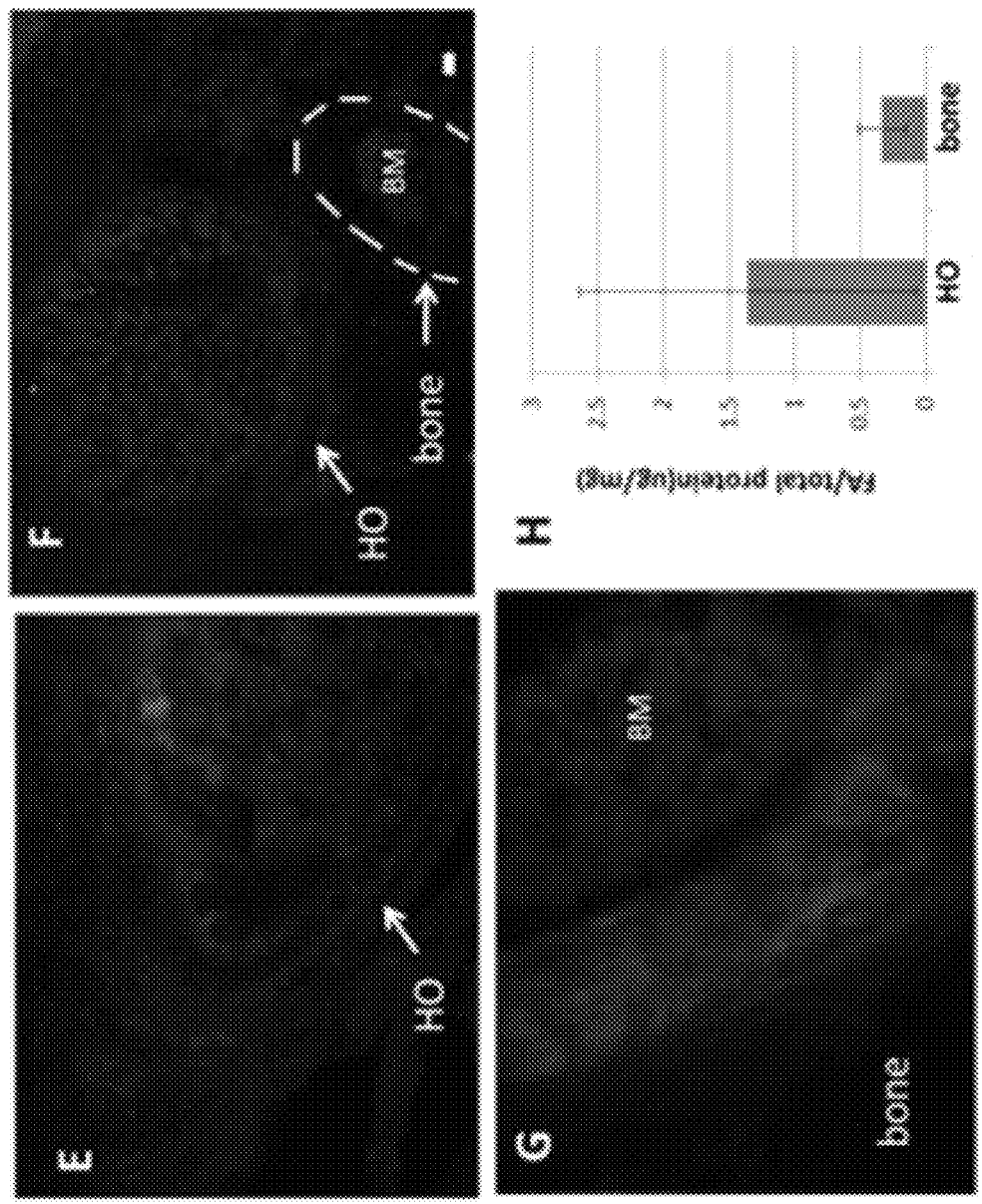
Figure 10:
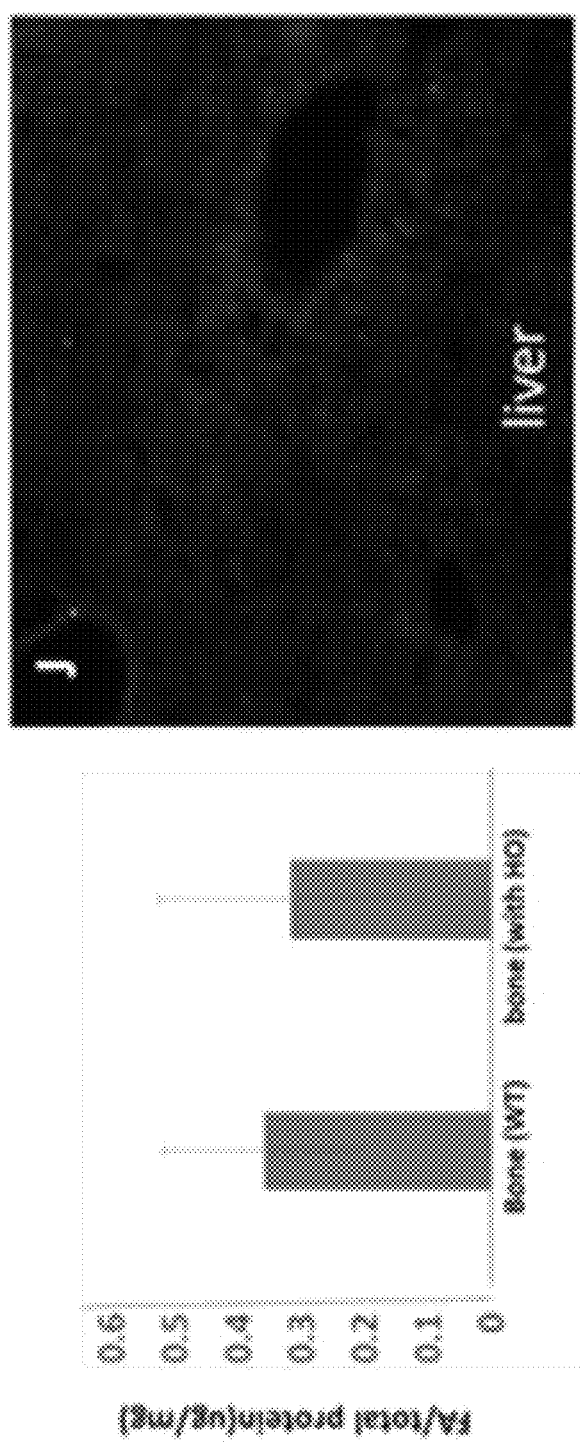

FA is specifically associated with HO. We stained the lesional sections of both WT and Nse-BMP4 mice at different stages post injury (p.i.). We found specific FA signals only in the lesional tissues in the sections from Nse-BMP4 mice (FIG. 10 & data not shown). Interestingly, based on the morphological features, the earliest specific staining emerged as small nodes inside the inner cores of the lesions apparently at late chondrogenic stage to early osteogenesis (see the difference between FIG. 10A&B), and as the lesions mature, the staining followed a stereotyped dynamic pattern, i.e., first transiently expended and then finally confined to the trabecular structure of the mature HO, and no significant FA staining was found in the surrounding unaffected tissues (FIG. 10C-E). The specific staining pattern in the lesional ECM coincident with the initiation of osteogenesis/ossification, which strongly suggested that FA is a specific biomarker of ossification associated with HO (FIG. 10A-E). Since previous studies have already indicated that FA is enriched in skeletal bone, it is interesting to compare the FA levels in HO and skeletal bone and clarify the potential interaction between HO and skeletal bone. We compared the FA levels through both IHC and ELISA. Based on pixel intensity in IHC, the FA level in HO is obviously higher than that in skeletal bone(>3 folds, data not shown) (F-H); however, comparison of the FA levels in HO and skeletal bone with ELISA assay found that the difference were statistically insignificant, even though the trend was still there (FIG. 11H), likely due to the heterogeneity of the HO tissues. We also compared the FA levels in skeletal bones from WT and Nse-BMP4 mice, but we did not find significant difference between these two groups either, Overall, this data suggests that the downregulation of FA in the circulation and the sequestration of FA in HO might still not significant enough to compete the FA away from skeletal bones in Nse-BMP4 mice.

Figure 11:
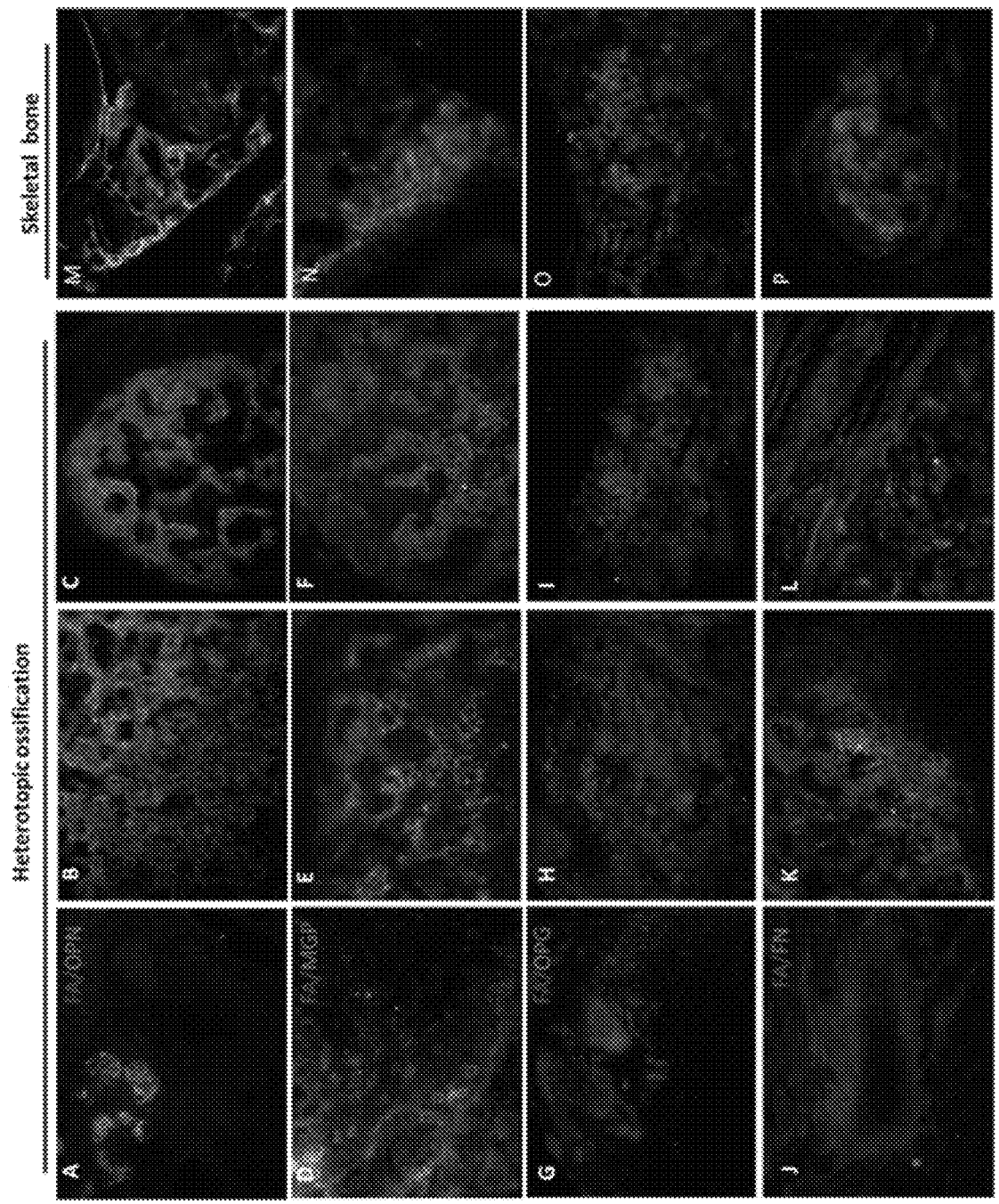
FIG. 11. Co-localization study suggested that FA is a specific ossification biomarker. Double staining of FA/OPN (top row), found that, FA was co-localized extensively with OPN; however, expression domain of FA was more limited than that of OPN, which also covered the chondrogenic region, at least in HO. In contrast, FA/MGP staining (2nd row) found that very limited co-localization was observed between FA and MGP, which is mainly associated with chondrogenic region in HO (D&E) and skeletal bone (N, note that MGP is highly expressed in articular cartilage). FA was mutually exclusive with OPG, a typical stromal and osteoclastic marker (3rd row). No significant co-localization was observed between FA and FN either(bottom row). A-L) are lesional sections at different stages of HO, and among these sections, 1st column (A,D,G&J) were from the early lesions (1 week p.i.), 2nd column (B,E,H&K) were from 2 weeks p.i.; 3rd column (C,F,I,L) were from 4 weeks p.i. M-P) are sections of normal skeletal bone.

Co-localization study further suggested that FA is a highly specific ossification biomarker. Double staining of FA with OPN (an acidic bone matrix ECM proteins secreted mainly by osteoblasts), MGP (a calcium-binding bone matrix proteins expressed mainly by chondrocytes), OPG (a secreted TNFR related protein expressed mainly by stromal cells and osteoclasts) and Fibronectin (a high-molecular weight glycoprotein of the ECM expressed mainly by fibroblasts) found that, in both HO and skeletal bone, FA was co-localized extensively with OPN (FIG. 11A-C&M), limited co-localized with MGP (FIG. 11D-F&N), mutually exclusive with OPG (FIG. 8G-I&O), and no significant co-localization with FN (FIG. 11J-L&P). Together, this data suggests that FA is probably the best ossification biomarker, at least better than the tested markers.

Figure 12:
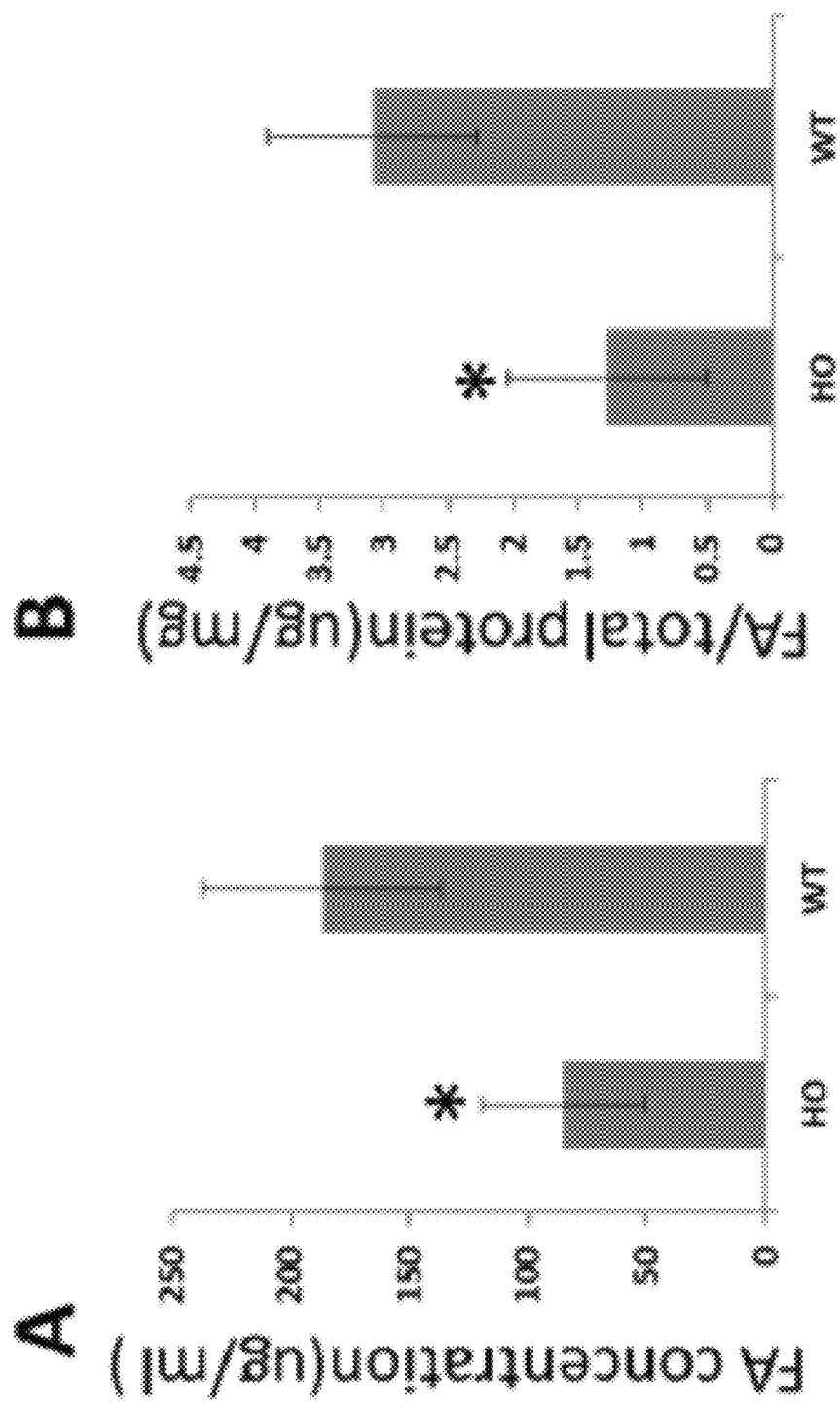
FIG. 12. Serum FA concentration was significantly decreased in the context of injury induced HO. A) Depictions of the absolute concentration of FA in the serum samples from Nse-MBP4 mice with HO and WT mice with the same injury 4 weeks p.i. B) Depiction of the normalized FA concentrations adjusted to the total serum protein concentration. *$P<01.05$ vs. control group.

Serum FA level was significantly decreased in mouse model of HO. We compared the FA levels in circulation in Nse-BMP4 and WT mice p.i. through ELISA and we found that both the absolute and the adjusted FA concentrations were significantly decreased in the Nse-BMP4 mice with HO, comparing with WT mice with the same injury (FIG. 12), which demonstrated the correlation between the downregulation of FA in circulation and HO.

Figure 13:
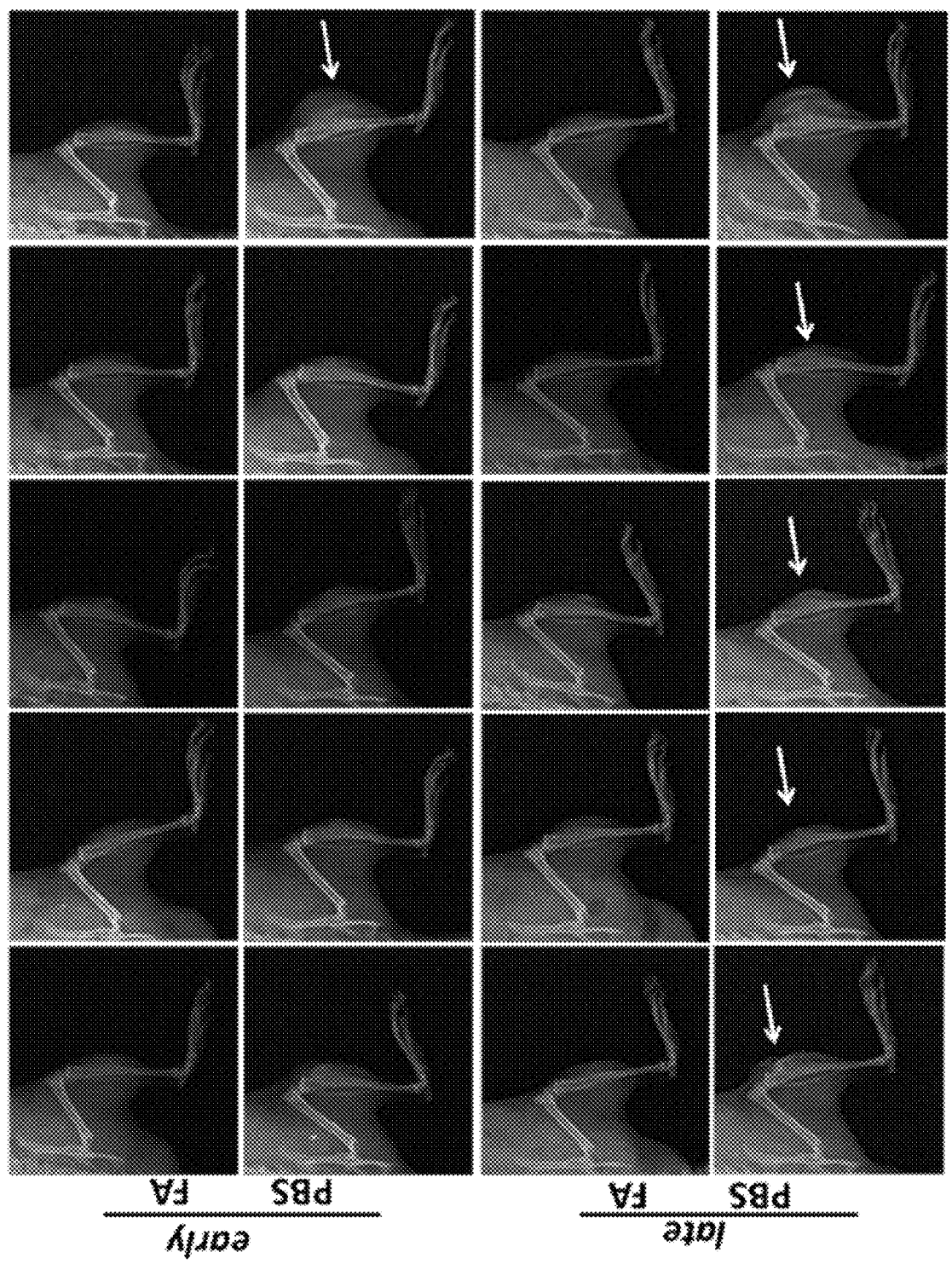
FIG. 13. Gain-of-function (GOF) of FA inhibited both the early tissue swelling and late HO. The early tissue swelling inhibited in FA treated mice (1st row), compared to the control mice treated with PBS (2nd row). The late HO was also inhibited in FA treated mice (3rd row), compared to the control mice treated with PBS (4th row). Arrows point to the HO in the control group.

Gain-of-function (GOF) of FA inhibited both the early tissue swelling and the final HO. To directly test the causal relationship, we performed GOF study of FA by injecting pure FA (20 mg/injection) intraperitoneally twice (one at 1 day p.i. and the other at 1 week after first injection). The weekly X-ray imaging demonstrated that both the early tissue swelling and the late HO formation were dramatically inhibited in FA treated mice, comparing to the control mice treated with PBS (FIG. 13).

Materials and Methods

Animals and injury models. Nse-BMP4 transgenic mice, described previously, express BMP4 under the control of promoter of neural-specific enolase (Nse). HO was induced by intramuscular injection of cardiotoxin (Sigma), according to previous reports. All animal experiments in this study were approved by the Animal Care and Use Committees of Northwestern University (Protocol: IS00001002).

IHC. Immunostaining for different markers were performed as previously described. Briefly, sections were pre-fixed with 4% paraformaldehyde in PBS. Nonspecific binding was blocked with 10% normal serum diluted in 1% bovine serum albumin (BSA; Jackson ImmunoResearch Laboratories, West Grove, PA) and 0.25% Triton X-100 (Sigma) for 1 h in room temperature. The sections then were incubated with primary antibodies diluted with 1% BSA+ 0.25% Triton X-100 at 4° C. overnight. After washing, the sections were incubated with appropriate secondary antibodies (Alexa Fluor 488, Alexa Fluor 594 conjugated antibodies, Thermo Fisher Scientific) diluted with 1% BSA+ 0.25% Triton X-100 in a dark at room temperature for 2 h, and counterstained with 4, 6-diamidino-2-phenylindole (1:5000). All fluorescent images were taken using ZEISS Axio Observer (Carl Zeiss, Germany). Signals from all channels were collected separately and overlaid in DPViewer.

ELISA quantification of FA. ELISA kit from R&D (cat #MFTA00) was used to quantify the expression of FA in serum and tissues of Nse-BMP4 and WT mice 4 weeks p.i., according to the manufacturer's instructions.

Gain-of-function study of FA. Nes-BMP4 (n=5) and WT (n=4) mice were treated with FA (Fetuin from fetal bovine serum, Sigma, F3004) (20 mg/mouse, 0.2 ml at 100 mg/ml) twice through Intraperitoneal (i.p.) injection starting id (day) p.i, and then a week after first injection; sex and age matched control Nse-BMP4 (n=5) and WT (n=4) mice were treated with PBS on the same schedule.

The sequence of bovine FA (*Bos Taurus*) is based on NCBI Reference Sequence: NP_776409.1 (SEQ ID NO:5)

```
  1 mksfvllfcl aqlwgchsip ldpvagykep acddpdteqa alaavdyink hlprgykhtl
 61 nqidsvkvwp rrptgevydi eidtlettch vldptplanc svrqqtqhav egdcdihvlk
121 qdgqfsvlft kcdsspdsae dvrklcpdcp llaplndsrv vhavevalat fnaesngsyl
181 qlveisraqf vplpvsvsve favaatdcia kevvdptkcn llaekqygfc kgsviqkalg
241 gedvrvtctl fqtqpvipqp qpdgaeaeap savpdaagpt psaagppvas vvvgpsvvav
301 plplhrahyd lrhtfsgvas vesssgeafh vgktpivgqp sipggpvrlc pgriryfki
```

The sequence of mouse FA [*Mus musculus*] based on NCBI Reference Sequence: NP_038493.1 (SEQ ID NO:6)

```
  1 mkslvlllcf aqlwgcqsap qgtglgfrel acddpeaeqv allavdylnn hllqgfkqvl
 61 nqidkvkvws rrpfgvvyem evdtlettch aldptplanc svrqltehav egdcdfhilk
```

```
121 qdgqfrvmht qchstpdsae dvrklcprcp lltpfndtnv vhtvntalaa fntqnngtyf 181 klveisraqn vplpvstlve fviaatdcta kevtdpakcn llaekqhgfc kanlmhnlgg 241 eevsvacklf qtqpqpanan avgpvptana alpadppasv vvgpvvvprg lsdhrtyhdl 301 rhafspvasv esasgetlhs pkvgqpgaag pvspmcpgri rhfki
```

The sequence of human FA [*Homo sapiens*] is based on NCBI Reference Sequence: NP_001341500.1 (SEQ ID NO:1)

```
  1 mkslvlllcl aqlwgchsap hgpgliyrqp ncddpeteea alvaidyinq nlpwgykhtl 61 nqidevkvwp qqpsgelfei eidtlettch vldptpvarc svrqlkehav egdcdfqllk 121 ldgkfsvvya kcdsspadsa edvrkvcqdc pllaplndtr vvhaakaala afnaqnngsn 181 fqleeisraq lvplppstyv eftvsgtdcv akeateaakc nllaekqygf ckatlseklg 241 gaevavtcmv fqtqpvssqp qpeganeavp tpvvdpdapp spplgapglp pagsppdshv 301 llaappghql hrahydlrht fmgvvslgsp sgevshprkt rtvvqpsvga aagpvvppcp 361 grirhfkv
```

The rationale for choosing only 2 injections was that, based on the reports, the in vivo half life of FA is about several days, and we expected the early intervention would likely prevent the downstream cascade that eventually cause the HO. X-ray images were took 2, 3, 4 weeks p.i. to determine the HO formation. micro-CT were performed 6 weeks p.i. to quantify the HO volume and density.

X-ray and micro-CT imaging. For X-ray, mice were anesthetized by 1% pentobarbital (150 µl i.p) and the images of radio-opaque HO were acquired by whole body x-ray examination at 38 kv, 28 mA, 30 seconds (Bruker, USA). To quantitatively measure HO volume, micro-CT (PerkinElmer, USA) was used with the setting parameters of 180° rotation, constant 90 kv voltage and voxel size 72 µm, and the 3D images were reconstructed by the software package of the system.

Statistical analyses. Data are reported as means±standard deviation. Statistical analyses between two groups were performed using Student's t-test via SPSS 16.0 (SPSS Science, Chicago, IL); statistical analyses between multiple groups were performed using one-way analysis of variance followed by the least significant difference post hoc test. P<0.05 was considered as statistically significant.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating and/or inhibiting heterotopic ossification in a subject in need thereof, the method comprising administering to the subject an effective amount of an immune checkpoint inhibitor to treat and/or inhibit heterotopic ossification in the subject, wherein the immune checkpoint inhibitor is selected from the group consisting of an anti cluster of differentiation 152 (CD152) antibody, an anti programmed cell death protein 1 (PD-1) antibody, an anti programmed death-ligand 1 (PD-L1) antibody, and combinations thereof.

2. The method of claim 1, wherein the subject has experienced traumatic injury prior to administering to the subject the effective amount of the immune checkpoint inhibitor to treat and/or inhibit heterotopic ossification in the subject.

3. The method of claim 1, wherein the subject has undergone surgery prior to administering to the subject the effective amount of the immune checkpoint inhibitor to treat and/or inhibit heterotopic ossification in the subject.

4. The method of claim 1, wherein the immune checkpoint inhibitor is the anti CD152 antibody.

5. The method of claim 1, wherein the immune checkpoint inhibitor is the anti PD-1 antibody.

6. The method of claim 1, wherein the immune checkpoint inhibitor is the anti PD-L1 antibody.

7. A method for treating and/or inhibiting heterotopic ossification in a subject in need thereof, the method comprising: (i) administering to the subject an effective amount of an immune checkpoint inhibitor to treat and/or inhibit heterotopic ossification in the subject, wherein the immune checkpoint inhibitor is selected from the group consisting of an anti CD152 antibody, an anti PD-1 antibody, an anti PD-L1 antibody and combinations thereof; and (ii) administering to the subject an effective amount of Fetuin-A to treat and/or inhibit heterotopic ossification in the subject, wherein the effective amount of the immune checkpoint inhibitor is administered to the subject before, concurrently with, or after the effective amount of the Fetuin-A is administered to the subject.

8. The method of claim 7, wherein the subject has experienced traumatic injury prior to administering to the subject the effective amount of the immune checkpoint inhibitor to treat and/or inhibit heterotopic ossification in the subject; and/or wherein the subject has experienced traumatic injury prior to administering to the subject the effective amount of the Fetuin-A to treat and/or inhibit heterotopic ossification in the subject.

9. The method of claim 7, wherein the subject has undergone surgery prior to administering to the subject the effective amount of the immune checkpoint inhibitor to treat and/or inhibit heterotopic ossification in the subject; and/or wherein the subject has undergone surgery prior to administering to the subject the effective amount of the Fetuin-A to treat and/or inhibit heterotopic ossification in the subject.

10. The method of claim 7, wherein the immune checkpoint inhibitor is the anti CD152 antibody.

11. The method of claim 7, wherein the immune checkpoint inhibitor is the anti PD-1 antibody.

12. The method of claim 7, wherein the immune checkpoint inhibitor is the anti PD-L1 antibody.

13. The method of claim 7, wherein the Fetuin-A or the variant thereof comprises an amino acid sequence of any of SEQ ID NOs:1-4, a processed form of any of SEQ ID NOs:1-4 lacking amino acids 1-18.

* * * * *